(12) United States Patent
Keusenkothen et al.

(10) Patent No.: US 9,677,014 B2
(45) Date of Patent: Jun. 13, 2017

(54) PROCESS AND APPARATUS FOR CONVERTING HYDROCARBONS

(75) Inventors: Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 242 days.

(21) Appl. No.: 13/994,229

(22) PCT Filed: Dec. 20, 2011

(86) PCT No.: PCT/US2011/066196
§ 371 (c)(1),
(2), (4) Date: Sep. 18, 2013

(87) PCT Pub. No.: WO2012/099676
PCT Pub. Date: Jul. 26, 2012

(65) Prior Publication Data
US 2015/0197696 A1    Jul. 16, 2015

Related U.S. Application Data

(60) Provisional application No. 61/434,417, filed on Jan. 19, 2011, provisional application No. 61/434,413, (Continued)

(30) Foreign Application Priority Data
Mar. 31, 2011    (EP) .................................. 111607602

(51) Int. Cl.
*B01D 3/00*    (2006.01)
*C07C 5/09*    (2006.01)
(Continued)

(52) U.S. Cl.
CPC ............. *C10G 55/04* (2013.01); *B01D 3/009* (2013.01); *B01J 19/245* (2013.01); *C07C 2/76* (2013.01);
(Continued)

(58) Field of Classification Search
CPC ...................................................... C10G 55/04
(Continued)

(56) References Cited

U.S. PATENT DOCUMENTS 1,134,677 A    4/1915   Heinemann
1,860,624 A    5/1932   Sauerwein
(Continued)

FOREIGN PATENT DOCUMENTS

BE    722895    10/1968
DE    875198    4/1953
(Continued)

OTHER PUBLICATIONS

Energy Fuels, 2007, 21(2), pp. 640-645.
(Continued)

*Primary Examiner* — In Suk Bullock
*Assistant Examiner* — Aaron Pierpont

(57) ABSTRACT

An apparatus and process are provided for processing hydrocarbon feeds. The process enhances the conversion of hydrocarbon feeds into conversion products, such as ethylene and propylene. In particular, the present techniques utilize two high-severity pyrolysis reactors integrated with another reactor type to convert hydrocarbons to other petrochemical products. The pyrolysis reactors recycle a portion of one of the reactor products to at least one of the pyrolysis reactors to further enhance the process.

15 Claims, 9 Drawing Sheets

Related U.S. Application Data filed on Jan. 19, 2011, provisional application No. 61/434,409, filed on Jan. 19, 2011, provisional application No. 61/434,411, filed on Jan. 19, 2011, provisional application No. 61/434,419, filed on Jan. 19, 2011, provisional application No. 61/434,410, filed on Jan. 19, 2011, provisional application No. 61/434,415, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.

| | | |
|---|---|---|
| *C08F 10/06* | (2006.01) | |
| *C08F 10/02* | (2006.01) | |
| *B01J 19/24* | (2006.01) | |
| *C10G 55/04* | (2006.01) | |
| *C07C 2/76* | (2006.01) | |
| *C10G 9/00* | (2006.01) | |
| *C10G 9/16* | (2006.01) | |
| *C10G 9/18* | (2006.01) | |
| *C10G 9/26* | (2006.01) | |

(52) U.S. Cl.
CPC .............. *C08F 10/02* (2013.01); *C08F 10/06* (2013.01); *C10G 9/002* (2013.01); *C10G 9/005* (2013.01); *C10G 9/007* (2013.01); *C10G 9/16* (2013.01); *C10G 9/18* (2013.01); *C10G 9/26* (2013.01); *B01J 2219/24* (2013.01)

(58) Field of Classification Search
USPC ........................................................ 585/286
See application file for complete search history.

(56) References Cited

U.S. PATENT DOCUMENTS

| | | |
|---|---|---|
| 2,319,679 A | 5/1943 | Hasche et al. |
| 2,678,339 A | 5/1954 | Harris |
| 2,692,819 A | 10/1954 | Hasche et al. |
| 3,024,094 A | 3/1962 | Coberly |
| 3,093,697 A | 6/1963 | Kasbohm et al. |
| 3,156,733 A | 11/1964 | Happel et al. |
| 3,242,223 A | 3/1966 | Nonnenmacher et al. |
| 3,419,632 A | 12/1968 | Sogawa et al. |
| 3,617,495 A | 11/1971 | Zimmerman, Jr. et al. |
| 3,644,555 A | 2/1972 | Nagy et al. |
| 3,839,484 A | 10/1974 | Zimmerman, Jr. et al. |
| 4,274,841 A | 6/1981 | Andresen et al. |
| 5,675,041 A | 10/1997 | Kiss et al. |
| 5,856,592 A | 1/1999 | Hagen |
| 6,049,011 A | 4/2000 | Kiss et al. |
| 6,121,503 A | 9/2000 | Janssen et al. |
| 6,177,600 B1 | 1/2001 | Netzer |
| 6,210,561 B1 | 4/2001 | Bradow et al. |
| 6,307,093 B1 | 10/2001 | Godwin et al. |
| 6,578,378 B2 | 6/2003 | Kaiser et al. |
| 7,045,670 B2 | 5/2006 | Johnson et al. |
| 7,115,789 B2 | 10/2006 | Kuechler et al. |
| 7,119,240 B2 | 10/2006 | Hall et al. |
| 7,138,047 B2 | 11/2006 | Stell et al. |
| 7,208,647 B2 | 4/2007 | Peterson et al. |
| 7,491,250 B2 | 2/2009 | Hershkowitz et al. |
| 7,815,873 B2 | 10/2010 | Sankaranarayanan et al. |
| 7,846,401 B2 | 12/2010 | Hershkowitz et al. |
| 7,943,808 B2 | 5/2011 | Hershkowitz et al. |
| 8,158,837 B2 | 4/2012 | Mamadov et al. |
| 8,440,070 B2 | 5/2013 | Keusenkothen |
| 2002/0000085 A1 | 1/2002 | Hall et al. |
| 2002/0098430 A1 | 7/2002 | Kawamura et al. |
| 2004/0002553 A1 | 1/2004 | Hall et al. |
| 2004/0192982 A1 | 9/2004 | Kuechler et al. |
| 2005/0065392 A1* | 3/2005 | Peterson ................... C07C 2/78 585/324 |
| 2007/0090018 A1 | 4/2007 | Keusenkothen et al. |
| 2007/0090019 A1 | 4/2007 | Keusenkothen et al. |
| 2007/0090020 A1 | 4/2007 | Buchanan et al. |
| 2007/0191664 A1* | 8/2007 | Hershkowitz et al. ........ 585/539 |
| 2008/0142049 A1 | 6/2008 | Onishi et al. |
| 2008/0300438 A1* | 12/2008 | Keusenkothen et al. ..... 585/400 |
| 2009/0198090 A1* | 8/2009 | Mamedov et al. ........... 585/324 |
| 2010/0130803 A1 | 5/2010 | Keusenkothen et al. |
| 2010/0292523 A1 | 11/2010 | Hershkowitz et al. |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2005/098948 | 10/2005 |
| WO | 2011/008389 | 1/2011 |
| WO | 2012/099679 | 7/2012 |

OTHER PUBLICATIONS

Watt, L., "The Production of Acetlene from Methane by Partial Oxidation", Thesis University OG British Columbia, Sep. 1, 1951, pp. 1-50.

SRI Consulting Process Economics Program "Acetylene" Report 16 (1966) and 16A (1982).

* cited by examiner

PROCESS AND APPARATUS FOR CONVERTING HYDROCARBONS

CROSS-REFERENCE TO RELATED APPLICATIONS

This application claims priority from (i) U.S. Provisional Application Ser. No. 61/434,413, filed Jan. 19, 2011, EP Application No. 11160760.2, filed on Mar. 31, 2011, and PCT/US2011/066196, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,411, filed Jan. 19, 2011, and PCT/US2011/066210, filed Dec. 20, 2011; (v) U.S. Provisional Application Ser. No. 61/434,415, filed Jan. 19, 2011, and PCT/US2011/066152, filed Dec. 20, 2011; (vi) U.S. Provisional Application Ser. No. 61/434,417, filed Jan. 19, 2011, and PCT/US2011/066186, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a process for converting hydrocarbons into unsaturated products, such as ethylene and propylene, which may be further processed into the other products. More particularly, the present techniques relate to apparatus useful for implementing the process, which enhances the conversion of hydrocarbons into these products through the use of integrated reactors.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products such as ethylene, propylene or polyolefins.

To convert hydrocarbon feeds into petrochemical or basic chemicals, chemical conversion processes may be utilized. These processes typically involve using thermal or catalytic reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas (e.g., ethane) and liquid (e.g., naphtha) feeds.

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., natural gas and/or aromatic gas oils).

To process these feeds, high-severity conditions (e.g., more severe operating conditions, such as higher temperatures) are generally involved to produce products having a higher value than the feed. High-severity conditions enable methane cracking and aromatic ring cracking, which do not occur at appreciable rates at typical low-severity conditions (e.g., conventional steam cracking conditions). At high-severity conditions, the primary products of thermal chemical conversion processes are acetylene and ethylene along with hydrogen ($H_2$) and coke, which may vary in proportion depending on the temperatures, pressures, residence times and feed type utilized in the conversion process. High-severity and low-severity conversion processes are typically based on different pyrolysis reactors, which may include pyrolysis alone or integrated with combustion chemistry. That is, the reactors may include pyrolysis chemistry (e.g., thermochemical decomposition of feed at elevated temperatures in the absence of oxygen) alone or in combination with combustion chemistry (i.e., exothermic chemical reactions between a fuel and an oxidant). These pyrolysis reactors can be divided into different types of high-severity, which include partial combustion, indirect combustion, arc process and thermal pyrolysis, for example. Each of these pyrolysis types differs in the means of generating and transferring the heat for the pyrolysis, which for simplicity are discussed below as techniques, which include the low-severity and high-severity.

The first technique is a partial combustion process or reactor. The partial combustion process burns part of the hydrocarbon feed to supply the heat to pyrolyse the remaining portion of the feed. The partial combustion reactor includes pyrolysis chemistry and combustion chemistry with both chemistries occurring at the same time and with the products of both chemistries being an integral part of the reactor product. An example of this process is German Patent No. 875198 and U.S. Pat. No. 7,208,647. Specifically, U.S. Pat. No. 7,208,647 describes a partial combustion process that utilizes partial oxidation to convert methane into ethylene. Due to the nature of this process, however, an air separation plant is typically required and combustion products (e.g., carbon monoxide (CO) and carbon dioxide ($CO_2$)) are significant components of reactor effluent that have to be managed. Further, this type of approach appears to be unsuitable for polymer grade ethylene used in the production of polyethylene due to the levels of CO and $CO_2$, which are both polyethylene catalyst poisons. As a result, the partial combustion process has certain limitations, such as the requirement to remove the high levels of combustion products and associated processing or additional processing equipment.

The second technique of pyrolysis reactor is the indirect combustion reactor. The indirect combustion process involves contacting combustion product with the feed to be cracked in the reactor. As such, this process involves pyrolysis and combustion chemistry, but typically the combustion chemistry may occur at a different time or location and the pyrolysis chemistry, while occurring in the presence of combustion products, proceeds in a largely non-oxidative environment, resulting in the products of the two chemistries being an integral part of the reactor product. In a process used by Hoechst (High Temperature Pyrolysis) in the 1960s, the thermal energy from a hot combustion product is used to crack a feed in direct contact. Examples of these types of reactors are described in G.B. Patent No. 834419 and German Patent No. 1270537. As another example, the Kureha/UCC process is similar, except that the primary purpose of this process is to make ethylene. In this process, which is described generally in U.S. Pat. No. 3,419,632, the hydrocarbon feed is a crude oil or a distillate having a boiling point less than (<) 1050° C. Further, U.S. Pat. No. 7,208,647 describes an indirect combustion process, which directly contacts the combustion gas with the feed to be cracked. Similar to the discussion for the partial oxidation process, this approach suffers from the same limitations of having to have an air separation plant and manage the combustion products This type of reactor and associated process also requires an expensive active quench step to stop the pyrolysis chemistry (e.g., water or oil).

The third technique of pyrolysis reactor is an arc reactor, which includes plasma arc reactors and electric arc reactors. This process typically involves only pyrolysis chemistry. Arc reactors are commercially limited and typically operated in a few small plants and described in U.S. Pat. No. 1,860,624. This process involving this type of reactor typically uses a water absorption process for recovery of acetylene, which was initially developed in the 1940s. The electric arc process utilizes electric power to heat a feed. As an example, U.S. Pat. No. 7,119,240 describes an electric arc reactor and process. The drawback of the arc process is the high cost of utilities, such as electricity, required to generate the "arc" or plasma. As a result, this process is limited to small units integrated with supplies of "cheap" electricity, such as a hydroelectric plants or nuclear facilities.

The fourth technique of pyrolysis reactors is a thermal pyrolysis reactor. Thermal pyrolysis reactors involve heating a solid material (e.g., by combustion) and using the heated solid material to crack the pyrolysis feed. In the thermal pyrolysis processes, the combustion products are typically maintained separate from the pyrolysis hydrocarbon products (e.g., via pyrolysis chemistry alone). This pyrolysis technique involves various different types of reactors, such as a regenerative reactor (e.g., as used in the Wulff process) and others. U.S. Pat. No. 7,119,240 describes an exemplary process for the conversion of natural gas into ethylene. In this process, natural gas is cracked in a furnace, actively quenched, and processed in a hydrogenation reactor to produce ethylene.

The "Wulff" reactor, as described in the IHS, SRI Consulting's Process Economics Program "Acetylene" Report Number 16 (1966) and 16A (1982) along with U.S. Pat. Nos. 2,319,679; 2,678,339; 2,692,819; 3,024,094, and 3,093,697, uses a reverse-flow pyrolysis reactor, which is typically operated at temperatures of <1400° C., to produce olefins and alkynes, such as acetylene. The pyrolysis feed is heated by refractories which have previously been heated by combustion reactions. The pyrolysis feed is cracked, and then cooled outside of the reactor. The relatively slow quenching is a characteristic of the Wulff process that leads to coke and soot formation from using inefficient indirect heat transfer (e.g., from checker brick). Coke formation in the reactor provides fuel during the combustion cycle and excess coke or soot may be alleviated by using a light feed, i.e., a hydrocarbon containing a high proportion of hydrogen. However, because the indirect heat transfer limits the rate of heat input in the Wulff process, certain pyrolysis feeds, such as methane, may not be economically processed, which limits the feed flexibility for this process. As a result, these reactors typically have limitations, such as poor heat transfer and greater soot generation resulting in poorer selectivity to desired products.

While the prior art describes using different pyrolysis reactors, these reactors described include various limitations, which reduce the efficiency of the process. Accordingly, it is desirable to provide a process that converts hydrocarbon feeds into olefins, such as ethylene, in an enhanced manner with high-severity reactors types being integrated together in an efficient manner.

SUMMARY

In an embodiment, the invention relates to a hydrocarbon conversion method comprising:

exposing a first pyrolysis feed in a first pyrolysis reactor to a peak pyrolysis gas temperature ≥1400.0° C. to produce a first reactor product, wherein the first pyrolysis feed has a hydrogen content ≥14.0 wt % based on the weight of hydrocarbon in the pyrolysis feed;

exposing a second pyrolysis feed in a second pyrolysis reactor to a peak pyrolysis gas temperature ≥1400.0° C. to produce a second reactor product having ≥0.5 wt % methane based on the weight of the second reactor product, wherein the second pyrolysis feed has a hydrogen content <14.0 wt % based on the weight of hydrocarbon in the pyrolysis feed; and separating hydrogen ($H_2$) from at least a portion of the first reactor product, wherein the second pyrolysis feed comprises at least a portion of the separated hydrogen;

separating methane from at least a portion of the second reactor product, wherein the first pyrolysis feed comprises at least a portion of the separated methane.

In another embodiment, this invention relates to an apparatus for processing hydrocarbons comprising:

a first pyrolysis reactor configured to expose a first pyrolysis feed to peak pyrolysis gas temperatures ≥1400.0° C. to produce a first reactor product;

a second pyrolysis reactor configured to expose a second pyrolysis feed to peak pyrolysis gas temperatures ≥1400.0° C. to produce a second reactor product; and a separation unit in fluid communication with the first pyrolysis reactor and configured to separate a recycle product from at least a portion of the first reactor product;

a mixing unit in fluid communication with the second pyrolysis reactor and the separation unit and configured to combine at least a portion of the recycle product with a second reactor feed to form the second pyrolysis feed.

In one aspect, one or more embodiments of the present techniques provide a process for enhancing the conversion of hydrocarbon feeds into conversion products, such as ethylene and propylene. In particular, the present techniques utilize a high-severity reactor integrated with another high-severity reactor, which are used to convert hydrocarbons to other petrochemical products in an enhanced manner. In particular, one of the high-severity reactors may utilize at least a portion of the reactor product to enhance the feed of the other pyrolysis reactor.

In one or more embodiments, a process for processing hydrocarbons is described. The process comprising exposing a first pyrolysis feed in a first pyrolysis reactor to peak pyrolysis gas temperatures ≥1400.0° C. to produce a first reactor product; exposing a second pyrolysis feed in a second pyrolysis reactor to peak pyrolysis gas temperatures ≥1400.0° C. to produce a second reactor product; and separating one or more of a first recycle product from at least a portion of the first reactor product and a second recycle product from at least a portion of the second reactor product; wherein one or more of (i) at least a portion of the first pyrolysis feed is derived from the second recycle product and (ii) at least a portion of the second pyrolysis feed is derived from the first recycle product.

In one or more embodiments, an apparatus for processing hydrocarbons is provided. The apparatus may include a first pyrolysis reactor, a second pyrolysis reactor, a separation unit and a mixing unit. The first pyrolysis reactor may be configured to expose a first pyrolysis feed to peak pyrolysis gas temperatures ≥1400.0° C. to produce a first reactor product, while the second pyrolysis reactor configured to expose a second pyrolysis feed to peak pyrolysis gas temperatures ≥1400.0° C. to produce a second reactor product. The separation unit in fluid communication with the first pyrolysis reactor and configured to separate a recycle product from at least the first reactor product, while the mixing unit in fluid communication with the second pyrolysis reactor and the separation unit and configured to combine at least a portion of the recycle product with a second reactor feed to form the second pyrolysis feed.

The process or apparatus may further include other aspects. For instance, the first pyrolysis reactor and second pyrolysis reactor may each be partial oxidation reactors, arc reactors or regenerative reverse flow thermal pyrolysis reactors. The process may further comprise combining a portion of the first reactor product with a portion of the second reactor product. The first pyrolysis feed may include ≥50 wt % of a first composition having a hydrogen content of the hydrocarbons in the first pyrolysis feed ≥14 wt %, while at least 50 wt % of the hydrocarbons in the second pyrolysis feed have a hydrogen content of the hydrocarbons that is ≤14 wt % or even ≤10 wt %. The first recycle product includes ≥30 wt % hydrogen in the first recycle product or ≥50 wt % hydrogen in the first recycle product, while the second recycle product includes one of ≥30 wt % methane in the second recycle product and ≥30 wt % ethane in the second recycle product, or specifically includes ≥50 wt % methane in the second recycle product.

The process may include various control mechanisms to manage the process or apparatus. For instance, the process may include measuring the hydrogen content of a second reactor feed prior to the second pyrolysis reactor; calculating a hydrogen deficiency amount based on the hydrogen content of the second reactor feed; and adjusting the hydrogen content of the second reactor feed to form the second pyrolysis feed based on the calculated hydrogen deficiency amount. Also, the process may include measuring temperature of a hydrocarbon feed; separating the hydrocarbon feed into the first pyrolysis feed and the second pyrolysis feed; and adjusting a separation level based at least partially on the measured temperature of the hydrocarbon feed.

In an embodiment, the first and/or second pyrolysis feed undergoes pyrolysis in at least one pyrolysis reactor, e.g., a regenerative reverse flow reactor that comprises a reactor body, wherein the reactor body forms a reaction region within the reactor body; a packing material disposed at least partially within the reaction region; and valve means (e.g., one or more poppet valve assemblies) coupled to the reactor body and in flow communication with the reaction region and controlling fluid flow of the at least a portion of the first pyrolysis feed between a location external to the reactor body and within the reaction region.

Figure 1A:
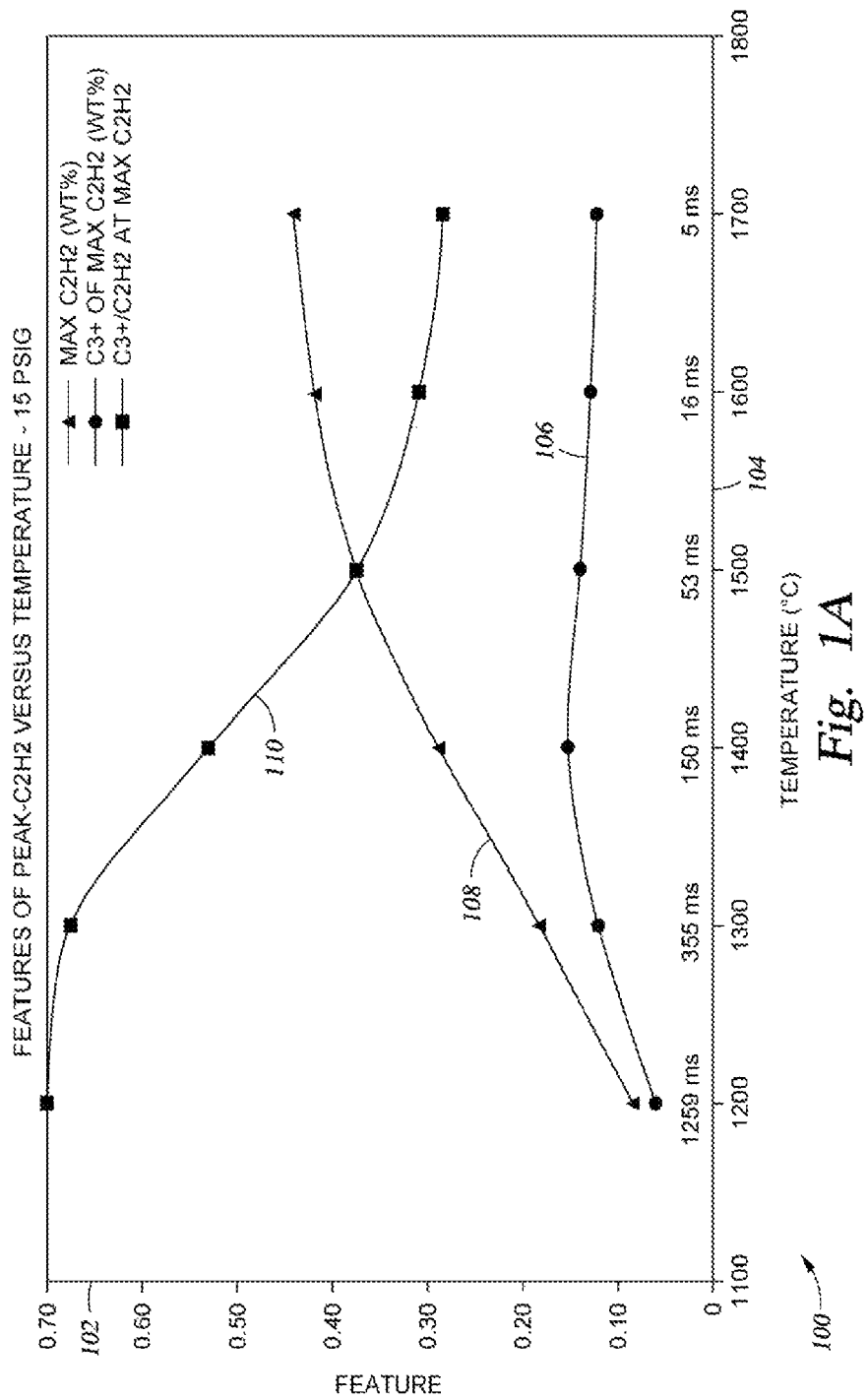
FIGS. 1A through 1F are diagrams of simulation results representing different ratios of reactor products produced at different temperatures and/or different pressures.

Although the invention is described in terms of a pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE EMBODIMENTS

In contrast to conventional techniques, the present techniques provide an enhanced process for conversion of feed containing hydrocarbons to olefins such as acetylene, ethylene and optionally polyethylene. The present techniques utilize two or more pyrolysis reactors at high severity to produce reactor products. In particular, a first pyrolysis reactor is configured to expose a first pyrolysis feed to high-severity operating conditions, while a second pyrolysis reactor is configured to expose a second pyrolysis feed to high-severity operating conditions, wherein at least a portion of the reactor products are recycled to the at least one (or both) of the pyrolysis reactors. These high-severity operating conditions (e.g., higher temperatures) may be utilized to crack feeds that are normally unreactive or react to low value products (e.g., degraded products) at lower temperatures. As a specific example, at temperatures greater than or equal to (≥) 1200.0° C., methane and aromatic components are partially cracked to yield unsaturated $C_2$+ compounds, typically acetylenes and ethylene. At temperatures ≥1400.0° C. or preferably ≥1540.0° C., aromatics and methane may be cracked at high conversion levels, with selectivity levels ≥50% to light gas products. The reactor product from the first pyrolysis reactor may have a hydrogen containing product separated from at least a portion of the first reactor product. At least a portion of the hydrogen containing product may be utilized to enhance the second pyrolysis feed for the second pyrolysis reactor. Similarly, the reactor product from the second pyrolysis reactor may have a light hydrocarbon containing product separated from at least a portion of the second reactor product. At least a portion of the light hydrocarbon containing product may be utilized to enhance the first pyrolysis feed for the first pyrolysis reactor. Similarly, the reactor product from the second pyrolysis reactor may have a light hydrocarbon containing product separated from at least a portion of the second reactor product. At least a portion of the light hydrocarbon containing product may be utilized to enhance the first pyrolysis feed for the first pyrolysis reactor.

In this type of configuration, the first pyrolysis reactor and the second pyrolysis reactor may include two or more high-severity reactors that are coupled together to produce reactor products. A hydrocarbon feed that is rich in hydrogen (e.g., a hydrogen rich hydrocarbon feed) may be fed to at optimum conditions to the first pyrolysis reactor. At least a portion of the first reactor product may be separated and combined with the feed being provided to the second pyrolysis reactor. In this manner, the second pyrolysis reactor may be used to crack portions of hydrocarbon feeds that are deficient in hydrogen or have a hydrogen content that is below a hydrogen threshold. As an example, a first recycle product (e.g., hydrogen gas ($H_2$)) may be separated from the first reactor product and combined with the hydrogen-deficient hydrocarbon feed to form a portion of the second pyrolysis feed. A hydrogen deficient hydrocarbon feed and a portion of the hydrogen gas ($H_2$) recycle from at least the pyrolysis of the first pyrolysis feed may be fed at optimum conditions to the second pyrolysis reactor. In addition, when the second pyrolysis reactor is used to crack hydrocarbon feeds that are deficient in hydrogen or have a hydrogen content that is below hydrogen threshold, the reactor product may contain light hydrocarbons (e.g., methane or ethane) that are hydrogen rich. These hydrogen rich hydrocarbon byproducts may be recycled to the first reactor. As an example, a second recycle product containing methane may be separated from at least a portion of the second reactor product and combined with the hydrogen-rich hydrocarbon feed to form the first pyrolysis feed, which may be fed to at optimum conditions to the first reactor. This recycle product may include ≥30 wt % methane, ≥30 wt % ethane or comprises one of ≥50 wt % methane. As a result, the conversion of the feed(s) is more efficient.

As a result, the present techniques provide a more efficient process to recover olefins by integrating high-severity pyrolysis reactors. To further explain the high-severity pyrolysis reactor and its associated products, various simulation results representing different ratios of reactor products produced at different temperatures and/or different pressures are provided. These simulations utilize certain feeds, such as methane, for simplicity, which are described further below, but the invention is not limited thereto.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_3^+$ in relationship to the yield of acetylene. The yield of $C_3^+$, as used herein, includes all $C_3^+$ products of the pyrolysis feed, whether those products emerge from the reactor or remain within the reactor as coke. $C_3^+$ includes, for example, products such as methyl acetylene, benzene and tar, and is specifically defined as including carbonaceous byproducts, such as coke. The maximum acetylene yield, the corresponding $C_3^+$ yield and the acetylene to $C_3^+$ weight ratio are described further in relation to temperature and residence time in FIGS. 1A and 1B and Table 1.

Figure 1B:
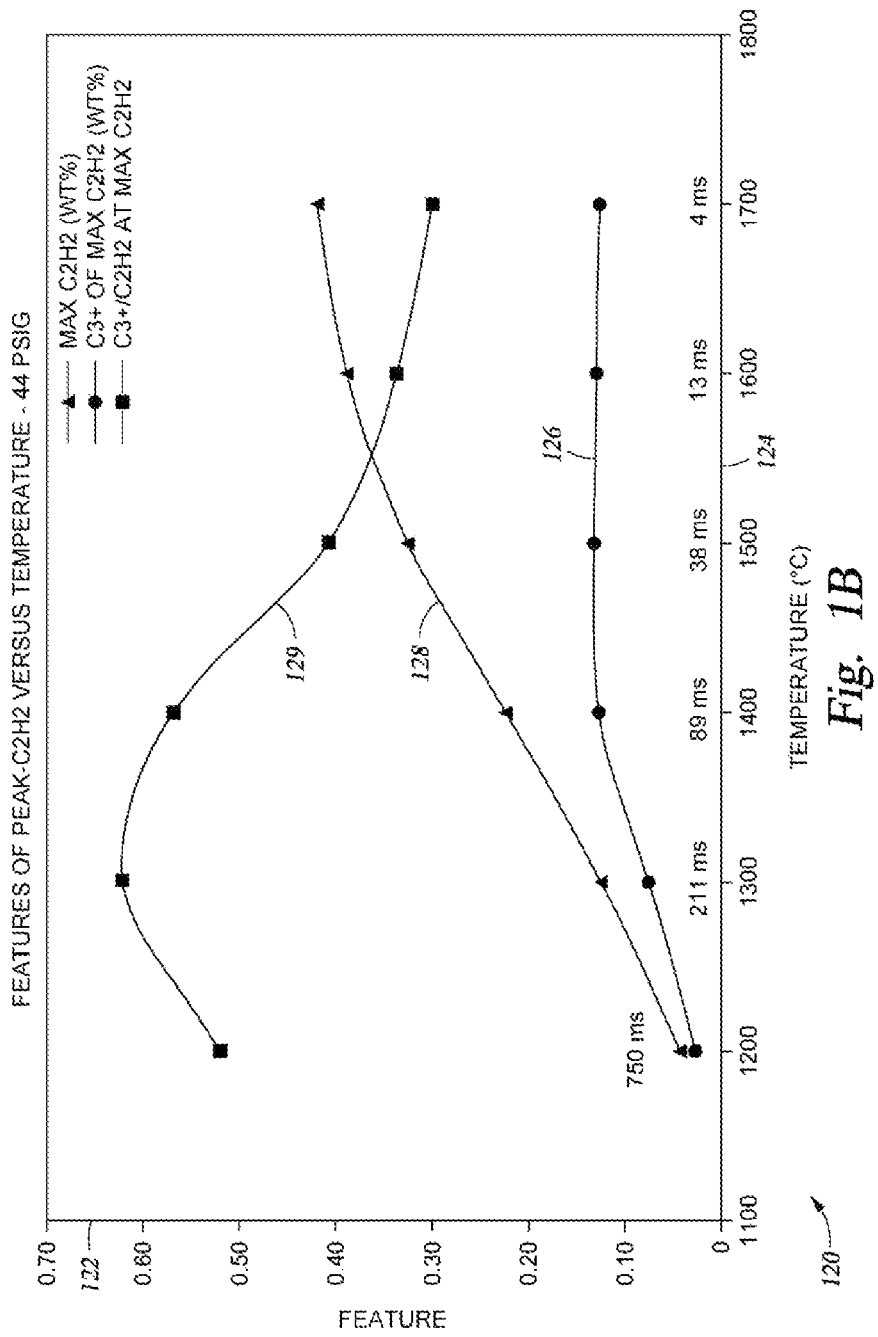

FIGS. 1A and 1B illustrate the simulation results for different ratios of reactor products produced at different temperatures from a methane feed. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at 14.7 pounds per square inch gauge (psig) (101 kiloPascal (kPag)) pressure for diagram 100 and at 44 psig (303 kPag) pressure for diagram 120. All hydrocarbon products larger than $C_2$ are considered as $C_3^+$ in this example and the product is the reaction product yield from the converted pyrolysis feed. In diagram 100, certain values for the maximum acetylene yield 108 in weight percent (wt %) of the product and corresponding $C_3^+$ yield 106 in wt % of the product and $C_3^+$ to acetylene weight ratio 110 of the product are shown along the Y-axis 102 for various temperatures (in ° C.) along the X-axis 104. The $C_3^+$ to acetylene weight ratio 110 has a peak between the temperatures of 1200° C. and 1400° C., which decreases at a slower rate as temperature increases from 1500° C. or 1540° C. Similarly, in diagram 120, certain values for maximum acetylene yield 128 in wt % of the product and corresponding $C_3^+$ yield 126 in wt % of the product and $C_3^+$ to acetylene weight ratio 129 of the product are shown along the Y-axis 122 for various temperatures (in ° C.) along the X-axis 124. The $C_3^+$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures from methane. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

TABLE 1

| Temperature (° C.) | 1200 | 1300 | 1400 | 1500 | 1540 | 1600 | 1650 | 1700 | 2200 |
|---|---|---|---|---|---|---|---|---|---|
| Max $C_2H_2$ (wt % of product) | 8.6% | 18.1% | 28.8% | 37.5% | 39.6% | 41.8% | 43.0% | 44.0% | 49.4% |
| Time of max $C_2H_2$(sec) | 1.259 | 0.355 | 0.150 | 0.053 | 0.035 | 0.016 | 0.009 | 0.005 | 0.00006 |
| $C_3^+$ (wt % of product) | 6.0% | 12.2% | 15.3% | 14.0% | 13.7% | 12.9% | 12.6% | 12.3% | 12.9% |
| $C_3^+/C_2H_2$ | 0.699 | 0.673 | 0.530 | 0.372 | 0.346 | 0.308 | 0.293 | 0.281 | 0.261 |

TABLE 1-continued

| Temperature (° C.) | 1200 | 1300 | 1400 | 1500 | 1540 | 1600 | 1650 | 1700 | 2200 |
|---|---|---|---|---|---|---|---|---|---|
| $C_2H_2$/unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of prod.) | 3.5% | 6.5% | 8.9% | 10.0% | 10.1% | 10.3% | 10.6% | 10.4% | 11.0% |

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % of the products. Residence time has a large impact on reactor volume (proportional to the reciprocal of residence time). As a result, a given unit of reactor may process more pyrolysis feed when the reactor temperature is high and residence time is low. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the pyrolysis feed.

Even though maximum acetylene ($C_2H_2$) yield increases for methane with increasing temperature, the $C_3^+$ yield is greatest for intermediate temperatures, such as 1400° C. Dividing $C_3^+$ yield by acetylene yield gives a selectivity parameter ($C_3^+/C_2H_2$) that indicates how much $C_3^+$, which is related to coke production, has to be managed per unit of acetylene produced. This selectivity parameter remains very high (e.g., ≥0.5) for temperatures below 1500° C., and drops into a lower section (e.g., less than or equal to (≤) 0.45 or ≤0.4) for temperatures at or above 1500° C.

For feeds containing high levels of aromatics or methane, temperatures below 1500° C. are not as effective for production of acetylene because of the high $C_3^+$ yields, the low acetylene yields, and the relatively long residence times (e.g., large reactor volumes) needed for processing. Conversely, considering the broad range of temperature cited for methane pyrolysis, there is an advantage to operating at temperatures above 1500° C., in terms of $C_2$ unsaturate ($C_2U$) yield and $C_2$ selectivity.

In addition, as shown in Table 1, pyrolysis of hydrogen-rich feed components of the pyrolysis feed, such as methane, result in substantial yield of hydrogen ($H_2$) gas. While the feed is composed of 20 wt % $H_2$ gas, the reactor product is composed on 24 wt % to 35 wt % $H_2$ gas. Surplus hydrogen may be calculated as the amount of $H_2$ remaining after conversion to some preferred product. In Table 1, surplus $H_2$ is calculated after subtracting the stoichiometric amount of $H_2$ utilized to convert the acetylene product to ethylene. For temperatures above about 1500° C., surplus $H_2$ remains roughly constant at about 10 wt % of the reactor product. Thus, the pyrolysis of hydrogen-rich hydrocarbon components of the pyrolysis feeds results in surplus $H_2$ that is available for use in the pyrolysis of hydrogen-deficient feeds or for other processes.

The high severity pyrolysis is also substantially impacted by ratio of hydrogen ($H_2$) gas to feed hydrocarbon carbon (C), as shown in Table 2, below. Pyrolysis, in this example, is carried out under isothermal conditions, for a feed containing methane gas and optionally hydrogen gas, at a temperature of 1550° C. and at 14.7 psig (101 kPag) reactor pressure. Residence time, in each case, is chosen to give 70% conversion of the methane feed. Table 2 lists the results, such as composition of the pyrolysis product (wt percent of total pyrolysis product) for operations at $H_2$/C levels between 0 and 5:

TABLE 2

| | $H_2/CH_4$ (molar ratio) | | | | | |
|---|---|---|---|---|---|---|
| | 0 | 1 | 2 | 3 | 4 | 5 |
| Residence time, sec | 0.004 | 0.007 | 0.011 | 0.014 | 0.018 | 0.021 |
| $CH_4$ Conversion: | 70.0% | 70.0% | 70.0% | 70.0% | 70.0% | 70.0% |
| $C_2U$, wt % | 28.2% | 34.7% | 36.0% | 35.1% | 33.4% | 31.6% |
| $C_3^+$, wt % | 28.2% | 15.6% | 9.3% | 6.1% | 4.4% | 3.3% |
| Hydrogen ($H_2$), wt % | 13.5% | 23.1% | 30.7% | 37.0% | 42.2% | 46.7% |
| $C_3^+/C_2U$ | 1.000 | 0.449 | 0.259 | 0.175 | 0.131 | 0.104 |
| relative $C_2$ productivity: | 509 | 280 | 168 | 111 | 78 | 57 |

As shown in Table 2, increasing hydrogen ($H_2$) diluent results has a small impact on $C_2U$ (acetylene and ethylene) yield, however increasing hydrogen diluent results in a substantial decrease $C_3^+$ yield and corresponding decrease in $C_3^+/C_2U$ weight ratio. Low hydrogen diluent levels may result in an unacceptably high level of $C_3^+$ yield and corresponding decrease in $C_3^+/C_2U$ weight ratio. High hydrogen diluent levels have a deleterious impact on reactor productivity because (a) the dilution reduces kinetic rates resulting in longer residence times (larger reactors) to achieve the same productivity, and (b) because $H_2$ dilution reduced the amount of hydrocarbon (and hence hydrocarbon products) that are carried in each volume of gas. These effects are reflected in the relative $C_2$ productivity entry on Table 2, which shows in relative terms the impact of hydrogen dilution on amount of $C_2$'s that are produced in a unit of reactor volume. High hydrogen dilution may also result in debits in process equipment outside of the pyrolysis reactor due to the larger volumes of gases that must be managed per unit of pyrolysis product produced. Thus there is an optimum in the amount of hydrogen diluent at moderate levels between 0 and 5. Thus, the present invention, by means of high temperature pyrolysis, achieves at low $H_2/C$ a level of $C_3+/C_2U$ that would otherwise require operating at high (and less economical) levels of $H_2/C$.

As shown in Table 3 below, conditions and yields for the pyrolysis of hydrogen deficient feeds may be different than those for the pyrolysis of hydrogen rich feeds shown in Table 1. A hydrogen deficient feed, in this example toluene having 8.7 wt % hydrogen content, is pyrolysed at 1445° C., 4 psig (28 kPag) pressure, for a residence time of 0.08 seconds with a hydrogen diluent at a level of 28 moles $H_2$ gas per mole of hydrocarbon carbon. In this toluene conversion case, a high $H_2/C$ molar ratio is employed to compensate for a low (1445° C.) pyrolysis temperature, while still achieving acceptable $C_3+/C_2U$ performance, thus illustrating features of toluene cracking. As indicated above, a more preferred operation would pyrolyze the toluene at higher temperature and lower $H_2/C$ molar ratio.

TABLE 3

| Pyrolysis of Toluene (8.7 wt % H) | | Products: wt % of toluene feed | | | wt/wt |
|---|---|---|---|---|---|
| Pressure (psig) | 4 | Methane | 26% | $C_3^+/C_2H_2$ | 0.351 |
| Temp (C.) | 1445 | Ethylene | 12% | $C_3^+/C_2U$ | 0.283 |
| Residence time, ms | 80 | Acetylene | 49% | E/A | 0.238 |
| $H_2/C$ | 28 | $C_3^+$ | 17% | | |
| | | $H_2$ | −5% | | |

As shown in Table 3, the pyrolysis results in a high conversion to acetylene (49 wt %) and ethylene (12 wt %), but also yields 17 wt % $C_3^+$ materials (mostly coke and tar). In contrast to the pyrolysis of hydrogen rich feed (Table 1), the hydropyrolysis of hydrogen deficient feed results in a consumption of hydrogen (from the $H_2$ diluent), and the production of methane (26 wt % of feed toluene) as a product. Accordingly, it is advantageous to recycle the excess hydrogen ($H_2$) gas that is produced from pyrolysis of a hydrogen-rich hydrocarbon feed to be used for the pyrolysis of the hydrogen deficient feed or other process. Further, it is advantageous to recycle the methane gas that is produced in the pyrolysis of a hydrogen deficient feed to be combined with the hydrogen-rich hydrocarbon feed.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures ≥1400° C. or preferably ≥1540° C., for example) aromatics and methane may be cracked at high conversion levels, with selectivity levels ≥50 wt % to light gas products. Also shown in table 1, at temperatures ≥1400° C., selectivity levels ≥50 wt % to light gas products are achievable. For example, at 1540° C., products of methane make up 67.8 wt % of the pyrolysis product, including $H_2$, $C_2$'s, and $C_3^+$. Thus, the selectivity to $C_3^+$ is 20 wt % (13.7 wt %/67.8 wt %), and the selectivity to lighter gas products is 80 wt %. Further, by varying the pressure from atmospheric to elevated pressures (e.g., up to 300 psig), ethylene to acetylene (E/A) weight ratios ≥0.1, ≥0.2, ≥0.4 or even ≥0.5 may be achieved. The variations of pressure at high-severity operating conditions are described below in Tables 4 and 5 and FIGS. 1C to 1F.

Table 4 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_3^+$ in this example and the product is the reaction product yield from the converted pyrolysis feed.

TABLE 4

| 70% Isothermal Conversion Data | | | | | | | | | | | |
|---|---|---|---|---|---|---|---|---|---|---|---|
| Temp | P | time | | Products (weight percent) | | | | | | | |
| (° C.) | (psig) | (sec) | Conv. | $H_2$ | $CH_4$ | $C_2H_2$ | $C_2H_4$ | $C_3^+$ | $C_2U$ | $C_3^+/C_2U$ | E/A |
| 1500 | 15 | 0.025 | 72% | 31.1 | 22.0 | 34.2 | 2.0 | 10.7 | 36.0 | 0.30 | 0.06 |
| 1500 | 36 | 0.025 | 73% | 31.1 | 21.7 | 32.7 | 3.1 | 11.3 | 36.0 | 0.32 | 0.10 |
| 1500 | 44 | 0.025 | 72% | 31.0 | 22.1 | 31.9 | 3.5 | 11.5 | 35.0 | 0.33 | 0.11 |
| 1500 | 59 | 0.025 | 71% | 30.7 | 23.3 | 30.3 | 4.1 | 11.6 | 34.0 | 0.34 | 0.14 |
| 1500 | 74 | 0.025 | 69% | 30.4 | 24.7 | 28.6 | 4.6 | 11.7 | 33.0 | 0.35 | 0.16 |
| 1500 | 103 | 0.025 | 65% | 29.7 | 27.9 | 25.4 | 5.4 | 11.5 | 31.0 | 0.37 | 0.21 |
| 1500 | 162 | 0.025 | 57% | 28.4 | 34.3 | 20.3 | 6.3 | 10.8 | 27.0 | 0.41 | 0.31 |
| 1650 | 15 | 0.0025 | 68% | 30.4 | 25.4 | 35.0 | 1.0 | 8.2 | 36.0 | 0.23 | 0.03 |
| 1650 | 36 | 0.0025 | 71% | 30.8 | 23.6 | 35.6 | 1.5 | 8.5 | 37.0 | 0.23 | 0.04 |
| 1650 | 44 | 0.0025 | 71% | 30.8 | 23.3 | 35.6 | 1.7 | 8.6 | 37.0 | 0.23 | 0.05 |
| 1650 | 59 | 0.0025 | 71% | 30.9 | 22.9 | 35.4 | 2.0 | 8.7 | 37.0 | 0.23 | 0.06 |
| 1650 | 74 | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table 4, as pressure increases from 15 psig (103 kPag) to 162 psig (1117 kPag), $C_2U$ yields in wt % of the product are roughly constant at about 33 wt % (+/−10 wt %) for 25 millisecond (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increase fourfold. Accordingly, the higher pressures tend to lead to higher E/A weight ratios. Further, the $C_3^+$ yields in wt % of the product at these different temperatures and pressures also remain relatively constant at 12% for 1500° C. and 9% for 1650° C. As a result, the $C_3^+$ to $C_2U$ weight ratio ($C_3^+/C_2U$) increases at slow rate with pressure at the lower temperature, while the higher temperatures provide a roughly constant $C_3^+$ to $C_2$ unsaturate weight ratio.

From this table, the yield of $C_2U$ (e.g., acetylene and ethylene) may be optimized for certain operating conditions. That is, a specific pressure, temperature and residence time may be utilized to optimize the distribution of $C_2U$ yield. These operating conditions may be characterized by the $C_3^+$ to $C_2U$ weight ratio along with an E/A weight ratio, which may be further explained in view of the FIGS. 1C and 1D.

Figure 1C:
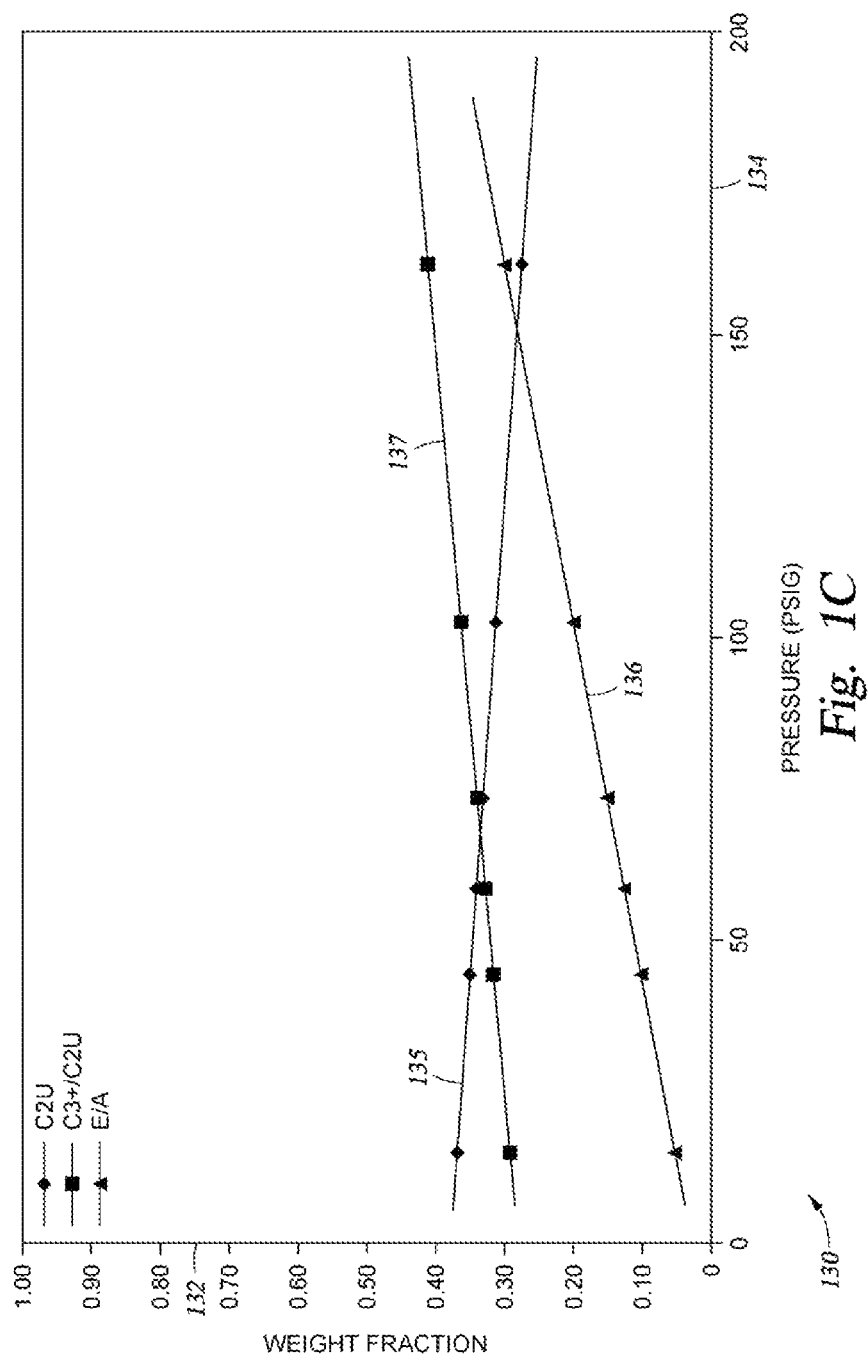
Figure 1D:
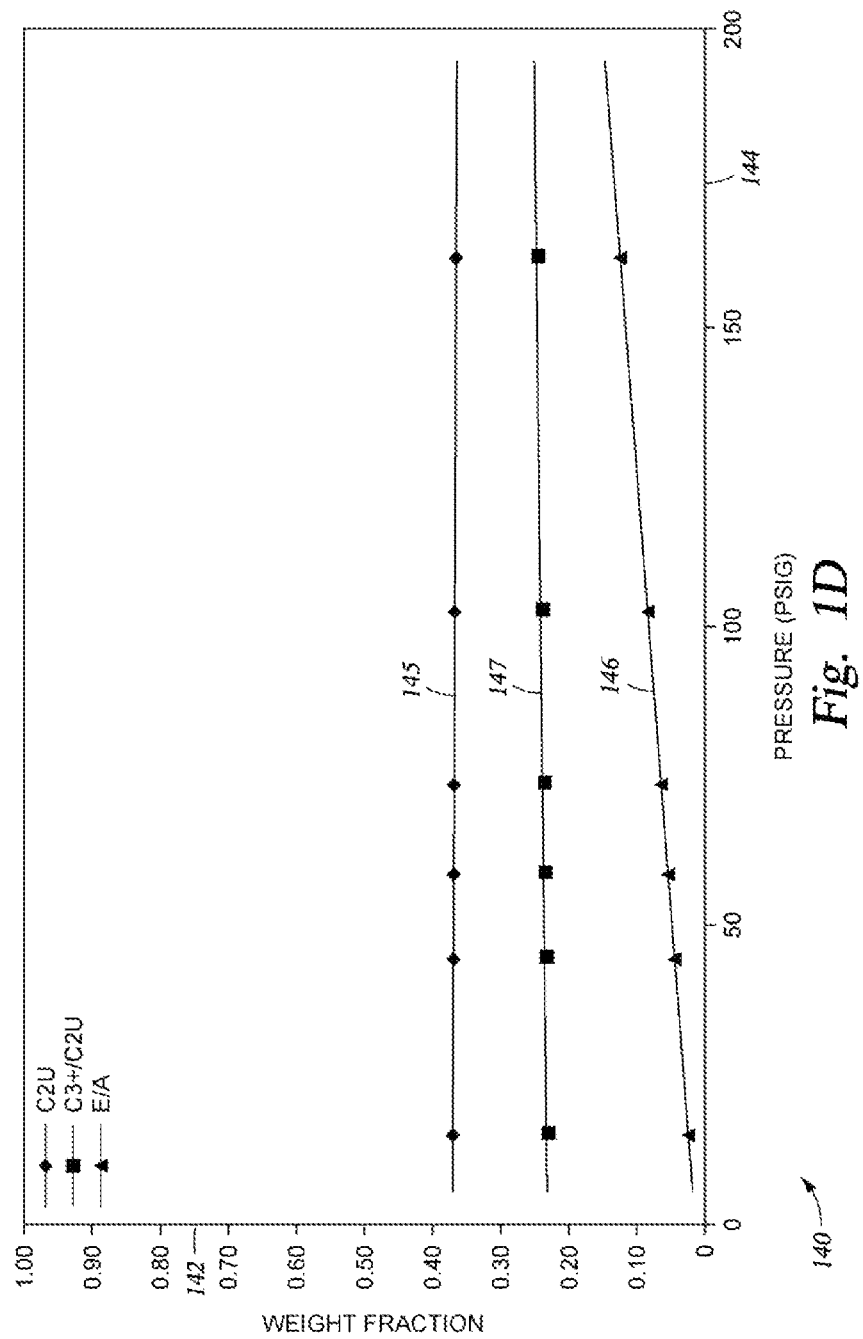

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_3^+$ in this example and the product is the reaction product yield from the converted pyrolysis feed. In diagram 130, certain values for a $C_2U$ yield 135 in wt % of the product, ethylene to acetylene weight ratio 136, and $C_3^+$ to $C_2U$ weight ratio 137 are shown in weight fraction (or weight ratio) along the Y-axis 132 for various pressures (in psig) along the X-axis 134. The ethylene to acetylene weight ratio 136 and $C_3^+$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_3^+$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_3^+$ to $C_2U$ weight ratio 147 are relatively constant with increasing pressure. As such, operating conditions of the thermal pyrolysis reactor may be adjusted to enhance the acetylene yield for a pyrolysis feed.

Further, as it may be appreciated, different types of thermal pyrolysis reactors may have different heat profiles. That is, some embodiments of thermal pyrolysis reactors may operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature ≥1000° C.), the pressure effect on selectivity is even more dramatic as shown in Table 5 below.

The variations of pressure at high-severity operating conditions for a regenerative reactor are described below in Table 5 and FIGS. 1E and 1F. Table 5 includes simulation results for different ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 3 psig (21 kPag) and 162 psig (1117 kPag). All products larger than $C_2$ are considered as $C_3^+$ in this example and the product is the reaction product yield from the converted pyrolysis feed.

TABLE 5

70% Regenerative Conversion Data

| Peak Temp (° C.) | Pres (psig) | time (sec) | Conv. | Products (weight percent) | | | | | | | |
|---|---|---|---|---|---|---|---|---|---|---|---|
| | | | | $H_2$ | $CH_4$ | $C_2H_2$ | $C_2H_4$ | $C_{3+}$ | $C_2U$ | $C_{3+}/C_2U$ | E/A |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 5, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_3^+$ levels at these different temperatures and pressures remain relatively constant at around 8 wt % for the two profiles. As a result, the $C_3^+$ to $C_2U$ weight ratio increases at slow rate for these different temperatures with the higher temperature providing roughly constant $C_3^+$ to $C_2U$ weight ratio, but the E/A weight ratio increases at a larger rate. Moreover, higher pressures do not have a significant impact on $C_3^+$ levels as the $C_3^+$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_3^+$ to $C_2U$ weight ratio along with an E/A weight ratio, which may be further explained in view of the FIGS. 1E and 1F.

Figure 1E:
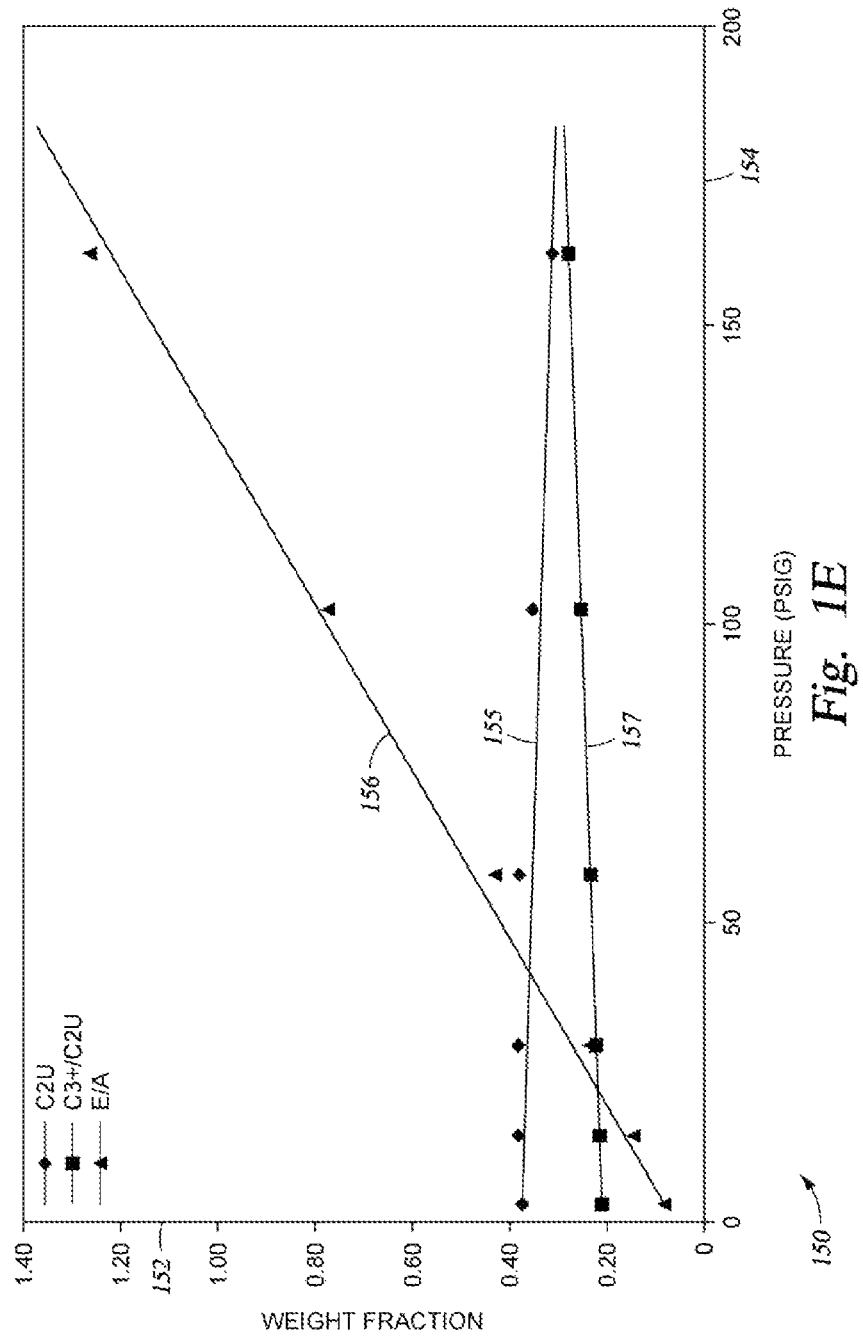
Figure 1F:
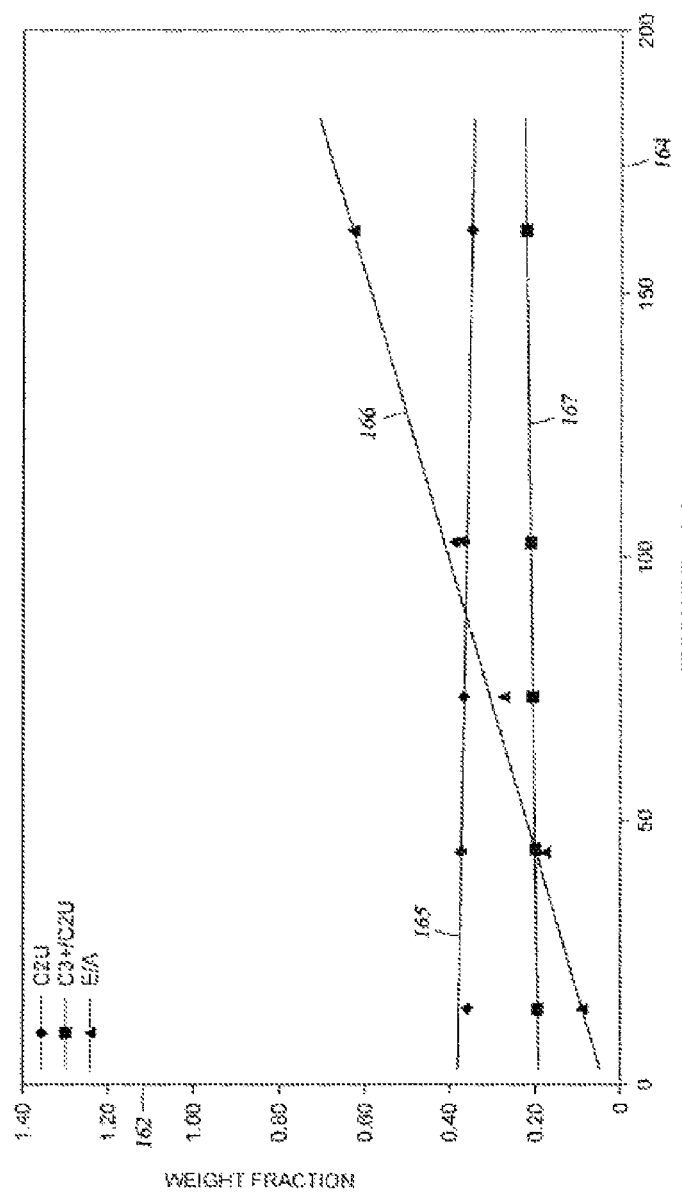

FIGS. 1E and 1F illustrate that the simulation results for different ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_3^+$ in this example and the product is the reaction product yield from the converted pyrolysis feed. In diagram 150, certain values for $C_2U$ yield 155 in wt % of the product, ethylene to acetylene weight ratio 156, and $C_3^+$ to $C_2U$ weight ratio 157 are shown in weight fraction (or weight ratio) along the Y-axis 152 for various pressures (in psig) along the X-axis 154. The ethylene to acetylene weight ratio 156 and $C_3^+$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_3^+$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_3^+$ to $C_2U$ weight ratio 157 are relatively constant with increasing pressure. As such, operating conditions of the regenerative thermal pyrolysis reactor may be adjusted to enhance the distribution of the ethylene yield and/or acetylene yield for a pyrolysis feed.

Although the E/A weight ratio continues to improve with increasing pressure, certain limiting factors may hinder higher pressure operations. For instance, eventually high pressure operating conditions may lead to unacceptable $C_3^+$ to $C_2U$ weight ratios and/or lower $C_2U$ yields. Further, equipment utilized in the system may be limited to certain pressure ranges. Accordingly, preferred operating pressures may include pressures ≥3 psig (21 kPag), ≥15 psig (103 kPag), ≥36 psig (248 kPag), ≥44 psig (303 kPag) or ≥103 psig (710 kPag), but may be ≤300 psig (2068 kPag), ≤163 psig (1124 kPag), or ≤150 psig (1034 kPag). As may be appreciated, these different pressures may be combined together to form different combinations depending on the specific configuration of equipment.

In addition, it may be beneficial to maintain longer residence times and lower temperatures to maximize E/A weight ratio. However, such residence times and temperatures result in higher weight ratios of $C_3^+$ to $C_2U$. Accordingly, the design and operating conditions may be adjusted to provide a balance between the E/A weight ratio and the $C_3^+$ to $C_2U$ weight ratio. That is, the thermal pyrolysis reactor may be operated lower temperatures to maximize the E/A weight ratio at an efficient and operable $C_3^+$ to $C_2U$ weight ratio. For instance, the operation of the pyrolysis unit, and hence operating conditions may be optimized based on objectives for the pyrolysis unit performance. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_3^+$ to $C_2$ unsaturate weight ratio. In another example, when the objective is a high E/A weight ratio, the pyrolysis reactor may be optimized by (i) using a regenerative reactor or other reactor having Gaussian-like temperature profile, (ii) increasing design operating temperature to be above a minimum level needed to achieve an acceptably low value of $C_3^+/C_2U$ (which may be referred to as a coke operability limit), and then (iii) increasing design operating pressure as much as possible given other reactor and system constraints. In another example, if the objective is a product with a minimal E/A weight ratio, the reactor may be optimized by (i) using a reactor that gives a isothermal temperature profile, (ii) operating the reactor at the lower end of the preferred pressure range, such as from about 3 psig (21 kPag) to about 59 psig (407 kPag), and (iii) increasing temperature as much as possible within the reactor materials constraints.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Unless otherwise stated, all percentages, parts, ratios, etc., are by weight. Unless otherwise stated, a reference to a compound or component includes the compound or component by itself, as well as in combination with other compounds or components, such as mixtures of compounds. Unless otherwise stated, all pressures are given as gauge (e.g., as pressure above ambient atmospheric pressure (e.g., psig)).

Further, when an amount, concentration, or other value or parameter is given as a list of upper preferable values and lower preferable values, this is to be understood as specifically disclosing all ranges formed from any pair of an upper preferable value and a lower preferable value, regardless whether ranges are separately disclosed.

The terms "convert" and "converting" are defined broadly herein to include any molecular decomposition, cracking, breaking apart, conversion, and/or reformation of organic molecules (hydrocarbons) in the feed, by means of at least pyrolysis heat, and may optionally include supplementation by one or more of catalysis, hydrogenation, diluents, and/or stripping agents.

As used herein, the expression "non-volatiles" may be defined broadly herein to mean substantially any resid, metal, mineral, ash, ash-forming, asphaltenic, tar, coke, and/or other component or contaminant within the feedstock that does not vaporize below a selected boiling point or temperature and which, during or after pyrolysis, may leave an undesirable residue or ash within the reactor system, which is difficult to remove. Noncombustible nonvolatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524, and D-2415.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_3^+$ product for pyrolysis selectivity. The term "$C_3^+$" means all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents).

As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as a weight percent of hydrocarbons in the respective feed. A hydrocarbon feed may have a hydrogen content in the range of 6 wt % (weight percent) to 25 wt %, 8 wt % to 20 wt % (e.g., not natural gas), or 20 wt % to 25 wt % (e.g., natural gas). The hydrogen content of hydrocarbon feeds, reactants and products for present purposes can be measured using any suitable protocol, e.g., ASTM D4808-01(2006) Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants. A hydrogen rich hydrocarbon feed is defined as a hydrocarbon feed having a hydrogen content of greater than a certain threshold level. This threshold level may be the preferred process product (in this case ethylene). Ethylene has a hydrogen content of 14 wt %, therefore the threshold hydrocarbon hydrogen level may be 14 wt %, and a hydrogen rich hydrocarbon feed would have a hydrogen content ≥14 wt %. Conversely, a hydrogen deficient hydrocarbon feed is defined as a hydrocarbon with a hydrogen content below the threshold level, and may have a hydrogen content of ≤14 wt %. Any hydrocarbon materials that may be hydrocarbon feeds (as defined above) may also be components of a hydrogen rich hydrocarbon feed or a hydrogen deficient hydrocarbon feed, as long as the overall (or average) hydrogen content of that hydrogen rich or deficient hydrocarbon feed meets the criteria for hydrogen content.

A hydrocarbon feed may be provided directly as a pyrolysis feed, may optionally be mixed with a diluent feed to form a pyrolysis feed, or may have a portion of the hydrocarbon feed removed (e.g., removal of components that are non-volatile at the operating conditions of the reactor) to form a pyrolysis feed. That is, the pyrolysis feed may be derived from the hydrocarbon feed. A pyrolysis feed may include hydrogen gas ($H_2$) in an amount that provides a preferred ratio of hydrogen (H) to carbon (C) considering all the hydrocarbon components and hydrogen ($H_2$) gas in the combined pyrolysis feed. The atomic hydrogen to carbon (H/C) ratio of the combined hydrogen ($H_2$) and hydrocarbon of the pyrolysis feed may be from 3:1 to 15:1, or values in between. Carbon in non-hydrocarbon species (e.g., $CO_2$) should be excluded for the purpose of this H/C calculation, as should hydrogen bound to oxygen (e.g., in $H_2O$). Alternatively, the ratio of hydrogen gas ($H_2$) moles to the total moles of carbon (C) in the hydrocarbon components of a pyrolysis feed may be set as a ratio of hydrogen to carbon ($H_2$/C) from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of a pyrolysis feed may result in a weight percent of total hydrogen in the pyrolysis feed that is greater than that in the hydrocarbon feed. For example, the weight percent of total hydrogen in a pyrolysis feed may be between 8 wt % and 54%.

As used herein, the expression "combustion feed" means the two or more individual feeds that are to be combined to form a combustion reaction or a combustion mixture of two or more of such feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$), and hydrogen. The combustion oxidant may include, but are not limited to, air, oxygen or mixtures thereof. Any of the combustion feed, fuel, or oxidant may additionally include non-combustible but volatile diluents such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent App. Pub. No. 20070191664.

The term "pyrolysis reactor", as used herein, refers to a system for converting hydrocarbons by means of at least pyrolysis chemistry. As used herein, the pyrolysis reactor may include pyrolysis chemistry alone (e.g., in the absence of oxygen for the conversion), or may also include combustion chemistry, including combustion chemistry that occurs along with the pyrolysis chemistry as in a partial combustion reactor. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 20070191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene is an endothermic process requiring addition of heat. The terms crack and cracking may be used interchangeably with the terms pyrolyse and pyrolysis. In a thermal pyrolysis reaction, ≥50%, ≥80%, or ≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as <50%, <20%, or <10% of the endothermic heat of pyrolysis.

The term "high-severity operating conditions" means pyrolysis conditions resulting in the conversion of the a pyrolysis feed comprising hydrocarbons to make a product having an acetylene content ≥10.0 wt % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time ≤0.1 seconds. Conversely, at temperatures below 1274° C., there are no times ≤0.1 seconds for which yields of acetylene reaches 10 wt % of the starting methane. A similarly-defined severity threshold temperature may be used to distinguish between high-severity and low-severity types of other reactors, such as partial combustion, indirect combustion, and arc processes. That is, if that reactor operation is capable of converting the hydrocarbon feed to ≥10% acetylene at a residence time of ≤0.1 seconds, that reactor is considered a high-severity reactor.

The term pyrolysis reactor type means one of the following pyrolysis reactor types of partial combustion, indirect combustion, arc process and thermal pyrolysis. The types of pyrolysis reactors can be divided into four different high-severity types of reactors: high-severity partial combustion, high-severity indirect combustion, high-severity arc process and high-severity thermal pyrolysis. These pyrolysis reactor types differ in the means of generating and transferring the heat for the pyrolysis.

According to one or more embodiments of the present techniques, an enhanced process, which utilizes two or more reactors of the same type, is provided for the production of $C_2U$ (e.g., acetylene and ethylene), which is useful for manufacturing polyolefins and other petrochemical products. The process may include various stages, such as feed preparation, pyrolysis, recovery and further processing, such as separation of the polymer grade monomer and polymerization to polyethylene. The pyrolysis reactors are high-severity pyrolysis reactors, such as high-severity partial combustion reactors, high-severity indirect combustion reactors, high-severity arc reactors and high-severity thermal pyrolysis reactors. The high-severity pyrolysis reactor may be utilized to expose a first pyrolysis feed to peak pyrolysis gas temperatures equal to or above 1400° C. or equal to or above 1540° C., for example.

Optionally, the high-severity pyrolysis reactor may have operating conditions that are below a specific selectivity threshold, such as a $C_3^+$ to acetylene weight ratio ≤0.5, ≤0.45, or ≤0.4. Operation at low levels of $C_3^+$/acetylene weight ratios is desirable to improve process economics and to improve process operability. Economics are improved by low $C_3^+$/acetylene weight ratio because $C_3^+$ products produced by high-severity pyrolysis are less valuable than the acetylene product. Further, operability is improved by low $C_3^+$/acetylene weight ratio because $C_3^+$ products may include substantial amounts of coke, which may hinder operations. Specifically, coke produced in excess amounts may result in an inability to maintain the fluid flow in certain pyrolysis reactor channels, and coke produced in excess amounts may result in heat release for certain reactors (e.g., during combustion or regeneration steps), which is greater than the heat amounts that can be used in the process or reactor.

Each high severity reactor type may have advantages or disadvantages relative to each other. For instance, partial oxidation reactors produce syngas or CO, as a major product, which has to be managed in the recovery stage. While arc reactors products are not contaminated by combustion products, the operation of these reactors is not economical unless a low cost electric power supply is available. Also, both the partial oxidation reactors and arc reactors may be amenable to resid containing feeds due to a close coupled active quench step, where the non-combustible non-volatiles are conducted away via the quench media. Thermal reactors may avoid certain limitations, such as the capital expense for air separation equipment, energy inefficiencies (e.g., heat loss) associated with an active quench utilized with other reactors, and impurities management, but may have problems with coking. Accordingly, these reactors may be advantageous when high syngas or CO yields are not preferred.

Regardless of the specific reactor type utilized, the reactor product from the reactors may be combined and processed together, as noted further below. That is, the reactor products may be combined to further reduce capital expense, while the present techniques provide an approach to enhance olefin yield from a feed. The reactor product or reactor effluent may be further processed to recover polyethylene, benzene, polyolefins or other products.

The present techniques may involve operating the two or more pyrolysis reactors that are both high-severity pyrolysis reactors. The operation of these pyrolysis reactors may include adjusting operational settings to adjust the pressure within the reactor and/or the temperature within the reactor. The operational settings may include increasing the heat generated by providing different combustion feeds to the respective pyrolysis reactor. Specifically, the reactors may operate at peak pyrolysis gas temperatures between 1200.0° C. and 2200.0° C., preferably between 1400.0° C. to 1900.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be in the range of 1540.0° C. and 2200.0° C. or 1600.0° C. and 1800.0° C. In addition, the process may involve pressures at atmospheric, ≥14.7 psig (101 kPag), ≥36 psig (248 kPag), ≥44 psig (303 kPag) or ≥103 psig (710 kPag), but may be 300 psig (2068 kPag), ≤163 psig (1124 kPag), or ≤150 psig (1034 kPag). For a regenerative reverse flow reactor, it may be operated to have a cycle time of the combustion step and the pyrolysis step that is between 0.5 second to 30 seconds. The present techniques may be further understood with reference to FIGS. 2 to 4, which are discussed below.

Figure 2:
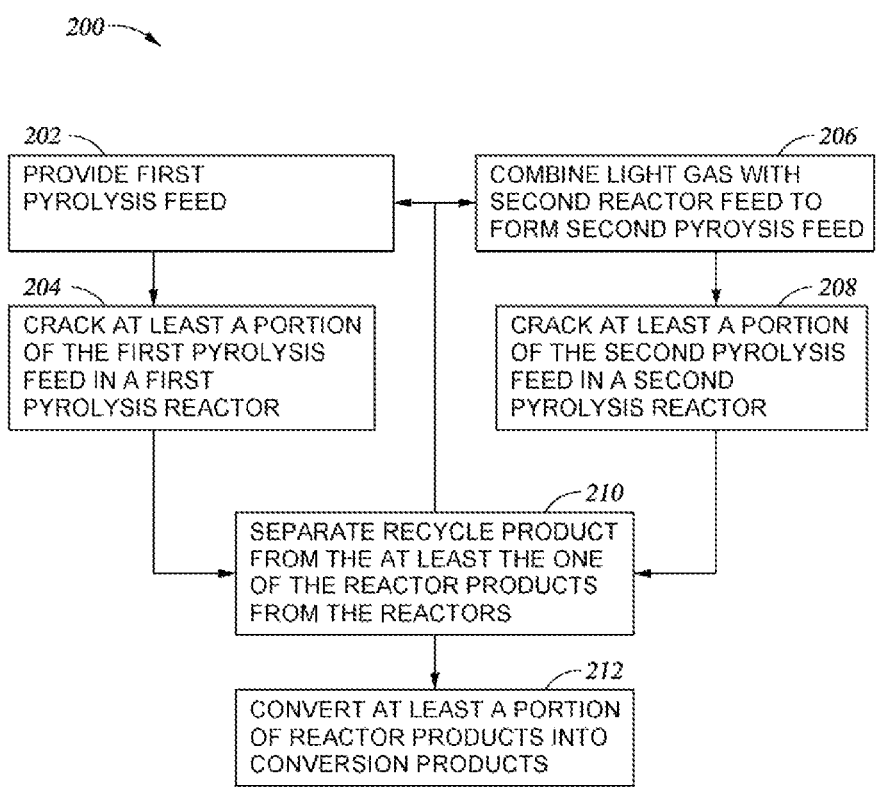
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process for the production of conversion products, such as ethylene, propylene, and/or polyolefins is described, which includes various stages. For instance, a feed preparation stage is described in blocks 202 and 206. A cracking stage is described in blocks 204 and 208, which involves exposing a first pyrolysis feed in a first pyrolysis reactor and a second pyrolysis feed in a second pyrolysis reactor to high-severity operating conditions. At least a portion of the reactor product from at least one of the reactors may be recycled to the other pyrolysis reactor to enhance the processing of the feed through the process. The remaining reactor products, which may contain an acetylene amount that reflects a pyrolysis $C_3^+$/acetylene weight ratio of ≤0.5, ≤0.45, or ≤0.4, may be processed together in an enhanced manner. The $C_2U$ (e.g., acetylene and ethylene) of the reactor products may represent ≥50 wt %, or ≥80 wt %, or preferably ≥90 wt % of the total $C_2^+$ gas phase components of the reactor products. Then, a recovery stage is described in blocks 210 and 212, which further processes the remaining reactor product or reactor effluent to recover a conversion product.

At block 202, a first pyrolysis feed is provided to a first pyrolysis reactor. The first pyrolysis feed may be derived from a first hydrocarbon feed including one or more of methane, natural gas, petroleum or petrochemical liquids and mixtures thereof, or other suitable hydrocarbon feeds. The first hydrocarbon feed may be a hydrogen rich feed having a hydrogen content ≥14 wt %, or may be between 14 wt % and 25 wt %. As a specific example, the first pyrolysis feed comprises ≥50 wt % of a first composition having a hydrogen content of the hydrocarbons in the first pyrolysis feed ≥14 wt %. The first hydrocarbon feed may be subjected to various feed preparation processes to form the first pyrolysis feed that is derived from the first hydrocarbon feed. That is, the feed preparation processes optionally include removal of impurities or contaminants from the hydrocarbon feed prior to providing the first pyrolysis feed to the first pyrolysis reactor. The feed preparation process may include mixing the first hydrocarbon feed with a diluent feed and/or processing the feed in one or more of condensate and water removal units, acid gas removal units (e.g., caustic or amine treater units), dehydration units (e.g., glycol units), nitrogen removal units, hydrogenation, demetalation, visbreaking, coking and/or vapor/liquid separators. The impurities or contaminants, which may include one or more of carbon dioxide, carbon monoxide, sulfur species, oxygenates and non volatiles (e.g., metal), may be conducted away from the process. As an example, at least a portion of the second reactor product, which may be a second recycle product, may be combined with a hydrocarbon feed to form the first pyrolysis feed (not shown on FIG. 2).

In block 204, the first pyrolysis feed is exposed to high-severity operating conditions in the first pyrolysis reactor. The exposure of the high-severity operating conditions may involve cracking a portion of the first pyrolysis feed into a first reactor product (e.g., first effluent) at temperatures above 1200° C. The reactor product includes one or more $C_2U$ and hydrogen ($H_2$), and optionally includes methane, ethane, methyl acetylene, diacetylene, and $C_3^+$ products (e.g., benzene, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. Further, the first pyrolysis reactor may include any one of the high-severity pyrolysis reactors, such as a high-severity partial combustion reactor, high-severity indirect combustion reactor, high-severity arc process reactor and high-severity thermal pyrolysis reactor. As a specific example, the first pyrolysis reactor may be a regenerative reverse flow reactor, as described in U.S. Ser. No. 11/643,541. Other embodiments may include a pyrolysis reactor, as described in U.S. Pat. No. 7,491,250, U.S. Ser.

No. 61/349,464 and U.S. Patent App. Pub. Nos. 20070144940, 20070191664 and 20080142409. For a regenerative reverse flow reactor, it may be operated to have a cycle time of the combustion step and the pyrolysis step that is between 0.5 second to 30 seconds. Regardless of the specific type of pyrolysis reactor, it may operate at peak pyrolysis gas temperatures between 1200.0° C. and 2200.0° C., between 1400.0° C. to 1900.0° C., or other suitable temperatures as noted above. Further, the process may involve pressures at atmospheric, ≥14.7 psig (101 kPag), ≥36 psig (248 kPag), ≥44 psig (303 kPag) or ≥103 psig (710 kPag), but may be ≤300 psig (2068 kPag), ≤163 psig (1124 kPag), or ≤150 psig (1034 kPag), as noted above. Also, for a regenerative reverse flow reactor, the pressure in the pyrolysis step may be similar or different to the pressure in the combustion step (e.g., at lower or higher pressure than the pyrolysis step).

At block 206, at least a portion of the first reactor product, which may be the first recycle product, may be combined with a second reactor feed to form the second pyrolysis feed. The second pyrolysis feed, which is provided to the second pyrolysis reactor, may include a hydrogen-deficient hydrocarbon feed. Accordingly, the feed may be subjected to various feed preparation processes to form the second pyrolysis feed from a second reactor feed, which may include similar processes to those described above for the first pyrolysis feed. The recycle product may include hydrogen ($H_2$), unconverted hydrocarbons, such as methane, or other suitable portions of the reactor product. The recycle product may include ≥30 wt % methane in the recycle product, ≥30 wt % ethane in the recycle product and/or ≥50 wt % methane in the recycle product.

In block 208, at least a portion of the second pyrolysis feed is exposed to high-severity operating conditions in the second pyrolysis reactor. Similar to the discussion above, the exposure of the high-severity operating conditions may involve cracking a portion of the second pyrolysis feed into a second reactor product, which may include one or more $C_2U$ and methane, and optionally includes hydrogen ($H_2$), ethane, methyl acetylene, diacetylene, and $C_3^+$ products (e.g., benzene, tars, soot, etc.). Further, the specific high-severity operating conditions of the second pyrolysis reactor may be different from those of the first pyrolysis reactor. For the second pyrolysis feed, at least 50 wt % of the hydrocarbons in the second pyrolysis feed may have a hydrogen content of the hydrocarbons that is ≤14 wt %, or at least 50 wt % of the hydrocarbons in the second pyrolysis feed have a hydrogen content of the hydrocarbons that is ≤10 wt %, for some embodiments.

At least a portion of the first reactor product and at least a portion of the second reactor product may be conducted away for storage or further processing. Optionally, one or more upgrading processes may be included in the recovery stage, as shown in blocks 210 and 212. For instance, the first reactor product from the first reactor and the second reactor product from the second reactor may be combined and subjected to various processes in the recovery stage in blocks 210 and 212. These reactor products may be combined in a combining unit, such as a manifold, piping connection, a portion of a compressor or other suitable unit. At block 210, a recycle product is separated from at least a portion of one of the reactor products and may also be separated from both of the reactor products. For example, the first reactor product from the first reactor may be subjected to a separation process alone to remove a recycle product or may be combined with at least a portion of the second reactor product into a combined reactor product prior to the separation process. Similarly, the second reactor product from the second reactor may be subjected to a separation process alone to remove a recycle product or may be combined with at least a portion of the first reactor product into a combined reactor product prior to the separation process.

The separation process may include one or more separation processes, such as a solid removal process, a light gas separation process and a heavy separation process, to produce the recycle products. The light gas separation process may include one or more separation processes to obtain different light gas products (e.g., a portion of the light gas in the first reactor product or combined reactor products) may be separated as light gas products and the remaining reactor product may form an acetylene-rich product. The light gas removal process may include different separation mechanisms along with a basic wash, for example caustic wash or amine scrubbing, to separate the light gas products away from the remaining reactor product. For other embodiments, the light gas separation mechanisms may include pressure swing adsorption, membranes, cryogenic distillation, electrochemical separation, liquid absorption, and/or liquid phase absorption and light gas desorbtion. The membrane inlet pressure or the pressure swing adsorption inlet pressure may be between 150 psig (1034 kPag) and 250 psig (1724 kPag), while the liquid phase absorption and light gas desorbtion may be performed at pressures between 50 psig (345 kPag) and 250 psig (1724 kPag). The light gas separation mechanisms may be used to separate hydrogen, carbon monoxide, methane, nitrogen or other light gases. The light gas products, such as hydrogen and/or methane, separated from the remaining portion of the reactor product may be used as a feed, a diluent feed for the first or second pyrolysis reactor, a feed stripping medium, as a fuel for the first pyrolysis reactor, or as a byproduct. For embodiments in which the products of the first reactor and second reactor are combined prior to the separation, the light gas product may include a light gas product (e.g., hydrogen ($H_2$)) produced from the first reactor and may include a light saturated hydrocarbon product (e.g., methane ($CH_4$)) produced from the second reactor. Thus, the products may be recycled to the feeds of the first and/or second reactors. For instance, the $H_2$ product may be combined with the feed to the second reactor, while the light saturated hydrocarbon product (e.g., $CH_4$) may be combined to the feed of the first reactor. The light gases may contain a fraction of the methane separated from the remaining reactor product or cracked stock. Separation may produce light gas products that are enriched in hydrogen ($H_2$) gas and/or products that are enriched in light saturated hydrocarbons, such as methane gas. Products that are $H_2$-enriched may be recycled to either pyrolysis reactor as diluent, for example, and/or may be recycled to the second pyrolysis reactor as diluent for hydrogen-deficient hydrocarbon feed. Products that are enriched in light saturated hydrocarbons, such as methane, may be recycled to either reactor as diluent, and/or may be recycled to the first pyrolysis reactor to be combined with the feed to that reactor (e.g., as a component of the hydrogen-rich hydrocarbon feed). $H_2$-enriched products may contain ≥30 wt % $H_2$, or ≥40 wt % $H_2$, ≥50 wt % $H_2$, ≥60 wt % $H_2$ or even ≥70 wt % $H_2$. Products that are enriched in light saturated hydrocarbons may contain ≥30 wt % $CH_4$, or ≥40 wt % $CH_4$, ≥50 wt % $CH_4$, ≥60 wt % $CH_4$ or even ≥70 wt % $CH_4$.

Further, in some embodiments, the light gas separation process may include additional stages or units to remove one or more of carbon dioxide ($CO_2$), hydrogen sulfide ($H_2S$), and water ($H_2O$) but also may include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below. Regardless, a portion of the $H_2$-containing recycle product is combined with the second reactor feed to form the second pyrolysis feed, as noted above in block 206. Optionally, a portion of the light hydrocarbon-containing product may be combined with the hydrogen-rich hydrocarbon feed to form the first pyrolysis feed, as noted above with respect to block 202.

At block 212, the remainder of the combined reactor product may optionally be provided to a conversion or upgrading process. The combined reactor product may be in liquid phase, vapor phase or a mixture thereof, and may be subjected to a conversion process that is performed by a catalyst. For instance, the conversion process may include an acetylene or methyl acetylene conversion process, which may include acetylenes hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, as is well known in the art. As another example, the conversion process may include a propylene conversion process.

Further, the conversion products, which may include ethylene or propylene, may optionally be provided to a purification or upgrading process. Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280,074; 5,288,473; 5,102,841; 4,956,426; 4,508,842; and EP Patent No. 0612753; and EP Patent No. 0012147.

Optionally, the upgraded product is conducted away for storage or for further processing, such as conversion into polyethylene or polypropylene. For instance, the purification process may include hydrogen separation, (multistage) distillation or refrigerated distillation including a demethanator tower and $C_2$ splitter. The products from the purification process may include hydrogen, CO, light hydrocarbons that also may be recycled to the first reactor, the second reactor and/or both. The purification process may produce light gas streams that are enriched in hydrogen ($H_2$) gas and streams that are enriched in light saturated hydrocarbons, such as methane gas. Streams that are $H_2$-enriched may be recycled to either pyrolysis reactor as diluent, for example may be recycled to the second pyrolysis reactor as diluent for hydrogen-deficient hydrocarbon feed. Streams that are enriched in light saturated hydrocarbons such as methane may be recycled to either reactor as diluent, and may be recycled to the first pyrolysis reactor as a component of the hydrogen-rich hydrocarbon feed. Further, olefin polymerization may include both the gas phase and solution polymerization methods, which conventional processes and may be employed in the practice of the present techniques. As an example, U.S. Pat. Nos. 6,822,057; 7,045,583; 7,354,979 and 7,728,084 describe different ethylene polymerization processes that may be utilized.

Optionally, the ethylene product may be provided for other processes or used commercially as a final product. These processes may include generating ethylene glycol or other products. As an example, the ethylene stream may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene product with a polyolefin-forming catalyst at a pressure and temperature effective to form the polyolefin product.

Beneficially, this configuration provides a more efficient process to recover olefins by integrating high-severity pyrolysis reactors. For instance, in this configuration, one of the enhancements is the flexibility in the hydrocarbon feed utilized for olefin recovery. That is, any hydrocarbon feed provided may be separated into different streams for the first pyrolysis reactor and the second pyrolysis reactor. For instance, the first pyrolysis feed may be derived from hydrocarbon feeds that have a hydrogen content above a certain threshold, while the second reactor feed may be derived from feeds with lower hydrogen contents feeds (e.g., heavy aromatic oils). These lower hydrogen content feeds may be combined with the recycle product (e.g., hydrogen product) from at least a portion of the first reactor product. By combining the lower hydrogen content feed with the recycle product, the resulting second pyrolysis feed may react in the process to provide $C_2U$ in the high-severity operating conditions. High-severity operating conditions, as provided in the present process, converts at high levels of aromatic containing feeds to valuable $C_2$ products. High-severity operating conditions, as provided in the present process, also converts aromatic containing feeds to methane and other light hydrocarbons which may be recycled to the first high severity reactor as a component of the first pyrolysis feed. By recycling the light hydrocarbon products from the first or second reactors back to the first reactor; the first reactor may be operated at conditions to maximize valuable $C_2U$ products. Various combinations of pyrolysis reactors may be envisioned, where the configuration of pyrolysis reactors may efficiently crack more of a hydrocarbon feed than other processes.

As a first example, the first and second pyrolysis reactors may be thermal pyrolysis reactors, such as reverse flow regenerative reactors. The first pyrolysis reactor may be utilized to crack light hydrocarbon feeds, such as propane or methane, while the second pyrolysis reactor may be used to convert waste products and/or fuel products, such as vacuum gas oils or aromatic fuel oils. In this configuration, a hydrogen product may be the recycle product separated from at least a portion of the first reactor product and recycled to the second pyrolysis reactor to enhance the hydrogen content of the feed. In this manner, the olefin yield may be enhanced by integrating the same reactor type to process the different feeds at lower operating cost. That is, this configuration may more efficiently process a hydrocarbon feed by using hydrogen produced from at least one of reactors, without the need for an additional hydrogen source.

As another example, the first and second pyrolysis reactors may be thermal pyrolysis reactors, such as reverse flow regenerative reactors. The first pyrolysis reactor may be utilized to crack light hydrocarbon feeds, such as methane or ethane, while the second pyrolysis reactor may be used to convert heavier hydrogen deficient hydrocarbons, such as fuel products, vacuum gas oils or aromatic fuel oils. In this configuration, a hydrogen product may be the recycle product separated from at least a portion of the first reactor product and recycled to the second pyrolysis reactor to enhance the hydrogen content of the feed to the second reactor. In addition, a light hydrocarbon product (e.g., methane) may be the recycle product separated from at least a portion of the second reactor product and recycled to the first pyrolysis reactor to maximize the valuable $C_2U$ and hydrogen produced from the first reactor. In this manner, the $C_2U$ yield may be enhanced by integrating two high-severity reactors to process the different feeds at lower operating cost. That is, this configuration may more efficiently process a hydrocarbon feed by using hydrogen produced from at least one of reactors, without the need for an additional hydrogen source.

Further, the integration of the pyrolysis reactors may provide the additional benefit that the recovery stage may be shared between the pyrolysis reactors. As another enhancement, the reactor products from the respective reactors may be combined to allow co-feeding of the reactor effluent to shared process equipment because the reactor products are similar. This efficient use of procession equipment may be tailored to specific reaction products of a given reactor combination. This may reduce the cost of installation, while providing more effective use of the hydrocarbon feed provided to the system.

Moreover, the proposed process provides various enhancements over previous techniques. For instance, the process provides flexibility in managing byproducts or contaminants That is, the high-severity pyrolysis reactor in the process may be operated in a manner that manages impurities does not involve additional stages to remove various contaminants, which improves the efficiency of the process. As an example, the process may manage impurities based on the high-severity operating conditions of the pyrolysis reactors. That is, the present techniques expose the pyrolysis feeds to high-severity operating conditions that may be used to manage the production of coke. These high-severity operating conditions may include peak pyrolysis gas temperatures $\geq 1200°$ C., or $\geq 1400°$ C. or $\geq 1540°$ C., for example. Further, the high-severity operating conditions may comprise a $C_3^+$ to acetylene weight ratio $\leq 0.5$, $\leq 0.45$, or even $\leq 0.4$. These high-severity operating conditions may be adjusted to manage $C_3^+$ production in the reactor process. As an example, certain impurities in the feed (e.g., asphaltenes and/or mercaptans) may be provided to the reactor and converted into acetylene or ethylene. By exposing the feed to these high-severity operating conditions, the $C_3^+$ product, which may include coke, tar and/or coke precursors, may be burned off within the reactor and removed from the process. As a result, feeds with higher asphaltene contents may be managed through the system without the concerns of coking in conventional processes. Other impurities, which may include but are not limited to sulfur and nitrogen containing compounds, oxygenates, Hg, salts, water, $H_2S$, $CO_2$, and $N_2$, may be removed as different products prior to or after the high-severity first pyrolysis reactor. That is, unlike other processes, the present techniques utilize operating conditions in the pyrolysis reactors to manage the impurities.

In addition, as noted above, by using high-severity conditions (e.g., higher temperatures) in the pyrolysis stage of the process, the present techniques may enhance $C_2$ selectivity for certain reactors in the system to manage the combined reactor product. That is, the pyrolysis stage may crack the pyrolysis feeds at residence times that are lower than other lower temperature processes. As a result, the pyrolysis feeds may be more efficiently cracked and the reactor sizes may be smaller (e.g., less capital expense and more efficient).

Moreover, when the pyrolysis reactors are regenerative reverse flow reactors, the configuration may be used to control the temperature of the reactor product at the reactor outlet to a temperature between 300° C. to 500° C. That is, the process may utilize passive quenching of the process to provide a reactor product that does not have to involve active quenching steps to lower the reactor product temperature.

Further, in one or more embodiments, a hydrocarbon feed may include non-volatiles, which are materials that are not in the gas phase (i.e. are components that are in the liquid or solid phase) at the temperature, pressure and composition conditions of the inlet to the pyrolysis reactor. Non-combustible non-volatiles (e.g., ash; ASTM D-189) are preferably limited to $\leq 2$ parts per million weight (ppmw) on hydrocarbon feed, more preferably $\leq 1$ ppmw. Combustible non-volatiles (e.g., tar, asphaltenes, ASTM D-6560) are may be present at concentrations below 5% of the hydrocarbon feed, preferably at concentrations below 1%, more preferably at concentrations below 100 ppmw, and most preferably at concentrations below 10 ppmw of the total feed to the pyrolysis reactor (e.g., first pyrolysis feed to second pyrolysis feed), as long as the presence of the combustible non-volatiles do not result in excessive (e.g., $\geq 2$ or $\geq 1$ ppmw) concentrations of non-combustible non-volatiles. As a first example, the hydrocarbon feed may comprise crude oil and crude oil components, which may be separated into different feeds for the different reactors. As a second example, the pyrolysis feed for one of the reactors may comprise substantially methane (e.g., $\geq 50$ wt %, $\geq 75$ wt %, or $\geq 90$ wt % of the pyrolysis feed).

In addition, for certain embodiments with the pyrolysis reactors being regenerative reverse flow reactors, air may be utilized instead of oxygen gas as part of the combustion process to generate heat for the pyrolysis feed because the combustion step is a separate step from the reaction step. Accordingly, using this type of reactor may reduce capital costs and operational costs by not requiring an oxygen feed (e.g., oxygen purification facilities) and reducing units that are utilized to remove combustion products from the reactor products.

Further, as noted above, the process may include other separation processes after blocks 204 and 208, such as a solid removal process, additional light gas separation process and a heavy separation process. The solid removal separation process may remove one or more bottom products comprising solids, such as higher boiling point materials (e.g., contaminates, solids or impurities) from the $C_2U$ in reactor product. The separation process may include a tar and/or solid removal process, compression, adsorption, distillation, washing, and drying of the remaining reactor product, and/or any combination of one or more of these processes. The additional light gas separation process may separate one or more different light gas products, as noted above. Optionally, a heavier product separation may conduct away a product of condensables from the remaining reactor product, which may be at least a portion of the first reactor product, second reactor product, or combined reactor product. The condensables may include vaporized liquids that condense, such as benzene, or are separated via cooled separations for example, adsorption, vapor liquid separators, flash drums etc.

The separation processes may optionally form an acetylene-rich product or stream and an acetylene-lean product or stream, which may involve separating different products from the reactor products from the respective reactors in the recovery stage. The acetylene-rich product may include ≥50 wt % of the acetylene from the reactor product, ≥70 wt % of the acetylene from the reactor product, ≥85 wt % of the acetylene from the reactor product, or even ≥95 wt % of the acetylene from the reactor product. The acetylene-lean product may include from 0 wt % to the remaining portion of the acetylene that is not in the acetylene-rich product. At least a portion of the reactor product may pass through one or more separations, such as a light gas separation or a heavier separation noted above, to remove different products from the remaining reactor product.

Also, the process may include compression of the combined reactor product. The compression may include compressors that operate at outlet pressures pressure from 50 psig (345 kPag) to 400 psig (2758 kPag), or more preferably from 150 psig (1034 kPag) to 300 psig (2068 kPag). Certain exemplary embodiments of this process are described further below in FIGS. 3 and 4.

Figure 3:
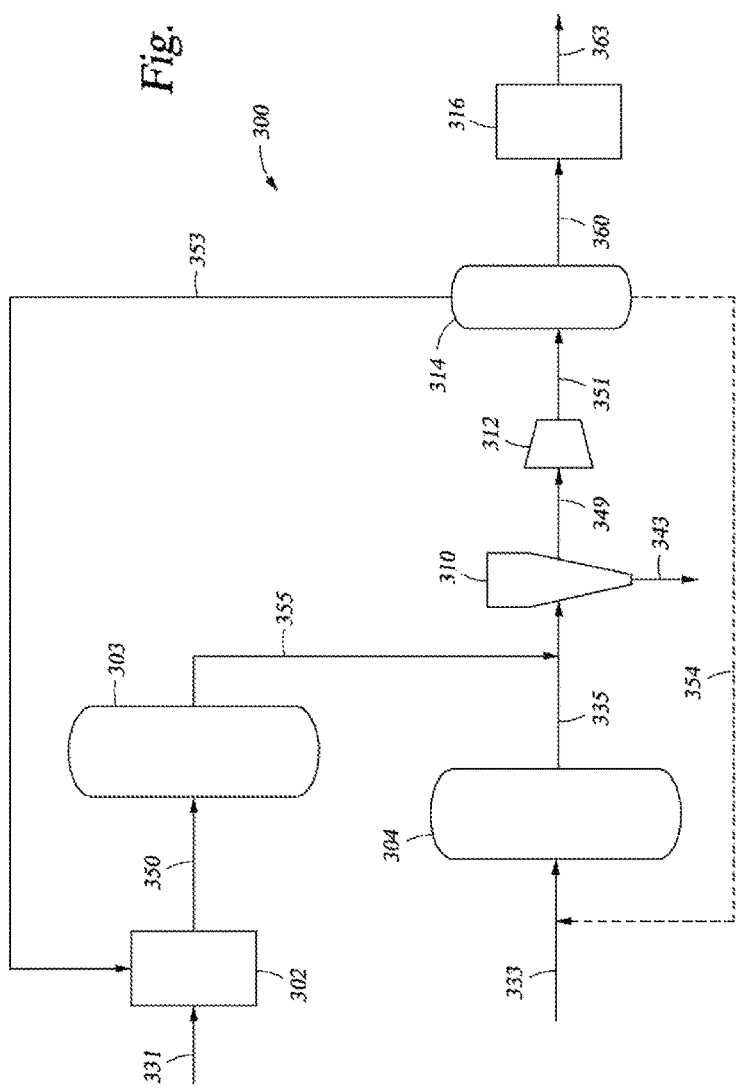
FIG. 3 is a simplified diagrammatic illustration of an exemplary process for converting a first pyrolysis feed and a second pyrolysis feed into conversion products in accordance with an embodiment of the present techniques.

FIG. 3 is a simplified diagrammatic illustration 300 of an exemplary process for converting a first pyrolysis feed and a second pyrolysis feed into a conversion product in accordance with an embodiment of the present techniques. In this illustration 300, a particular configuration of unit operations (i.e. units) are coupled together to convert pyrolysis feeds into conversion products. These units may include a mixing unit 302, a first pyrolysis reactor 304, a second pyrolysis reactor 303, a solid removal unit 310, a compressor 312, a product separation unit 314 and a converter 316. In particular for this configuration, the cracking stage may include the first pyrolysis reactor 304 and the second pyrolysis reactor 303, which are operated at high-severity operating conditions (e.g., at peak pyrolysis gas temperatures above 1400° C.). The recovery stage may include the solid removal unit 310, the compressor 312, the product separation unit 314 and the converter 316, while the feed preparation stage may include the mixing unit 302. The process is now explained in more detail.

A first pyrolysis feed, which is derived at least in part from a hydrogen-rich first hydrocarbon feed, for example, comprising methane, ethane, propane and/or other suitable hydrocarbon feed, is provided via line 333 to the first pyrolysis reactor 304. The hydrocarbon components of the first pyrolysis feed may have a hydrogen content of 14 wt % to 25 wt % of the hydrocarbon components of the of the first pyrolysis feed, 14 wt % to 20 wt % (e.g., not methane), or 20 wt % to 25 wt % (e.g., natural gas). Optionally, a diluent feed may be provided to adjust the hydrogen content of the pyrolysis feed to adjust the hydrogen content above a certain threshold. The diluent feed may include $H_2$, water or a lighter hydrocarbon, which lighter hydrocarbon is preferably a hydrocarbon with a high hydrogen content. The diluent may be provided as a recycle product; may be provided via line 354, which may include $H_2$, methane or other lighter hydrocarbon, such as a hydrocarbon with a high hydrogen content. The pyrolysis feed may be adjusted to have an atomic H/C ratio within a predetermined range (e.g., from 3:1 to 15:1), as noted above. Alternatively, for hydrogen-rich hydrocarbon feeds, the ratio of hydrogen gas ($H_2$) moles to the total moles of carbon (C) in the hydrocarbon components of the pyrolysis feed may be set as a ratio of hydrogen to carbon ($H_2$/C) from 0.0 or 0.1 to 5.0, such as 0.0, 0.1, 1.0, 2.0, 3.0, 4.0, 5.0, or values in between.

The first pyrolysis reactor 304, as noted above in FIG. 2, may include any high-severity pyrolysis reactor, or may preferably include a regenerative reverse flow reactor. Accordingly, the first pyrolysis reactor 304 may have different piping configurations to provide combustion feed (e.g., fuel) and the first pyrolysis feed separately, depending on the specific configuration.

The first reactor product from the first pyrolysis reactor 304 is conducted away via line 335 to the solid removal unit 310 and other recovery stage units. The solid removal unit 310 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the separation. The solid-liquid phase of the reactor product from the first reactor may be conducted away from solid removal unit 310 as a bottoms product, which may be a bottoms stream, via line 343. The bottoms product may include carbon black, soots, and/or heavy aromatic oils and/or tars. If the bottoms product is "dry", it may be handled via filtration or electrostatic separation; if sticky or wet, it may be better handled via washing (oil or water) or absorption. The bottoms product may be recycled to the second pyrolysis reactor or may be used as a fuel (in the first and/or second pyrolysis reactor). The remaining portion of the reactor product may be withdrawn from the solid removal unit 310 as an overhead stream via line 349 and passed to the compressor 312.

A second reactor feed, such as fuel oil (e.g., atmospheric resid), or other hydrogen deficient hydrocarbon feed, is provided via line 331 to the mixing unit 302. The mixing unit 302 combines the second reactor feed and the recycle product to form the second pyrolysis feed. The mixing unit may include a piping connection, a vessel, a manifold or a portion of the second pyrolysis reactor 303 that is used to mix the second reactor feed with the recycle product and provide it via line 350. The second reactor feed may have a hydrogen content of 6 wt % to 14 wt %, and may include components, as described above with respect to hydrocarbon feed. The recycle product may be provided via line 353, which may include $H_2$, water or a lighter hydrocarbon, such as a hydrocarbon with a high hydrogen content. The recycle product may be used to adjust the hydrogen content of the hydrocarbons in the second pyrolysis feed to be above a certain hydrogen threshold. For example, the second reactor feed may be combined with a diluent, such as the recycle product, which may result in the second pyrolysis feed having at least 50 wt % of the hydrocarbons in the second pyrolysis feed having a hydrogen content of the hydrocarbons ≤14 wt %, or even ≤10 wt %. In this example, the diluent provides the remaining portion of the hydrocarbons in the second pyrolysis feed, which may be from 0 wt % to 50 wt % of the hydrocarbons in the second pyrolysis feed (e.g., the remaining hydrocarbons). The mixture may optionally be adjusted with the same or other diluent feed to further adjust the hydrogen gas ($H_2$) content such that the ratio of hydrogen (H) to carbon (C) considering all the hydrocarbon components and hydrogen ($H_2$) gas in the combined pyrolysis feed falls within a predetermined H/C range, such as between 3:1 and 15:1, as noted above.

The second pyrolysis reactor 303, as noted above, may include another high-severity pyrolysis reactor that is the same type as the first pyrolysis reactor 304. Accordingly, the second pyrolysis reactor 303 may have different piping configurations to provide combustion feed (e.g., fuel) and the second pyrolysis feed separately, depending on the specific configuration. The second effluent or reactor product from the second pyrolysis reactor 303 is conducted away via line 355 to the solid removal unit 310, and/or other recovery stage units. These reactor products may be combined prior to or within the solid removal unit 310, within a combining unit (not shown), such as a manifold within lines 335 and 355, prior to the solid removal unit 310.

The compressor 312 may receive the vapor product from the solid removal unit 310, which is the remaining portion of the first reactor product, along with at least a portion of the second reactor product and compress the reactor products. The compressed reactor products may be provided via line 351 to the product separation unit 314. The compressor 312 may compress one or more of the remaining reactor products to a pressure from 50 psig (345 kPag) to 400 psig (2758 kPag), or more preferably from 150 psig (1034 kPag) to 300 psig (2068 kPag). For other embodiments, the pressure may be adjusted for hydrogen ($H_2$) removal (e.g., pressure swing adsorption, hydrogen membrane and/or cryogenic distillation, electrochemical separation) and acetylene hydrogenation.

The product separation unit 314 may include one or more separation units, such as a light gas separation unit and a heavy separation unit, to produce one or more recycle products. One recycle product is separated from compressed reactor product and provided via line 353 to the mixing unit 302. As noted above in block 210 of FIG. 2, the product separation unit 314 may include different separation mechanisms along with a basic wash, for example caustic wash or amine scrubbing, to separate the light gas products away from the remaining reactor product. Specifically, the product separation unit 314 may include pressure swing adsorption, membranes and/or cryogenic distillation, electrochemical separation and liquid absorption. The product separation unit 314 may separate hydrogen and/or methane as the recycle product. Separation may produce light gas streams that are enriched in hydrogen ($H_2$) gas and streams that are enriched in light saturated hydrocarbons, such as methane gas. Streams that are $H_2$-enriched may be recycled either pyrolysis reactor as diluent, for example may be recycled to the second pyrolysis reactor as diluent for hydrogen-deficient hydrocarbon feed. Streams that are enriched in light saturated hydrocarbons, such as methane may be recycled to either reactor as diluent, and may be recycled to the first pyrolysis reactor as a component of the hydrogen-rich hydrocarbon feed. The remaining reactor product (e.g., the acetylene rich product) is provided via line 360 to the converter 316.

Optionally, the converter 316 may receive the remaining reactor product (e.g., $C_2U$ steam or products comprising acetylene and ethylene) from the product separation unit 314. The converter 316 may include different units depending on the desired conversion product, such as an acetylene converter or propylene converter. If the converter 316 is an acetylene converter (A/C), it selectively hydrogenates the acetylene to ethylene without significantly hydrogenating the ethylene to ethane. The acetylene converter may operate at feed levels ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % to ethylene. The acetylene converter may include an optional finishing acetylene converter to convert remaining levels of acetylene at 100 wt % conversion of the acetylene. This finishing acetylene converter may be in fluid communication with the one or more units, such as the acetylene converter or other units downstream of the converter 316. The acetylene converter may include a hydrogenation unit, and optionally may further include a compressor, stream recycle components, desorption unit and/or separation unit.

The conversion product may be passed to a purification unit (not shown) via line 363, which may include a demethanator tower (to remove $H_2$, $CH_4$, $N_2$ and CO) and a $C_2$ splitter to remove ethane and upgrade ethylene to polymer grade ethylene. The purification unit may also include $C_2$ or $C_3$ refrigeration train, compression and additional distillation towers. This purification unit may separate the conversion product from the acetylene converter into one or more products and an upgraded product, such as an ethylene stream. The one or more products may include different light gas products (e.g., hydrogen, carbon monoxide, nitrogen, methane, and the like) or heavier products (e.g., ethane and $C_3^+$ streams). A portion of the recovered products may be recycled for processing again in the first pyrolysis reactor or second pyrolysis reactor, such as methane and/or hydrogen. Purification may produce light gas streams that are enriched in hydrogen ($H_2$) gas and streams that are enriched in light saturated hydrocarbons such as methane gas. Streams that are $H_2$-enriched may be recycled either pyrolysis reactor as diluent, for example may be recycled to the second pyrolysis reactor as diluent for hydrogen-deficient hydrocarbon feed. Streams that are enriched in light saturated hydrocarbons such as methane may be recycled to either reactor as diluent, and may be recycled to the first pyrolysis reactor as a component of the hydrogen-rich hydrocarbon feed. Further, if the upgraded product is an ethylene stream, it may be provided to the ethylene polymerization unit.

Further, an optional ethylene polymerization unit may be a catalytic reactor, which may include a gas catalyst and/or a liquid catalyst. The process may involve a catalyst, solvent and the feed stream, as discussed above. Further, a portion of the acetylene in the reactor product may optionally be combined with other process steps to form other products in other embodiments. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

Figure 4:
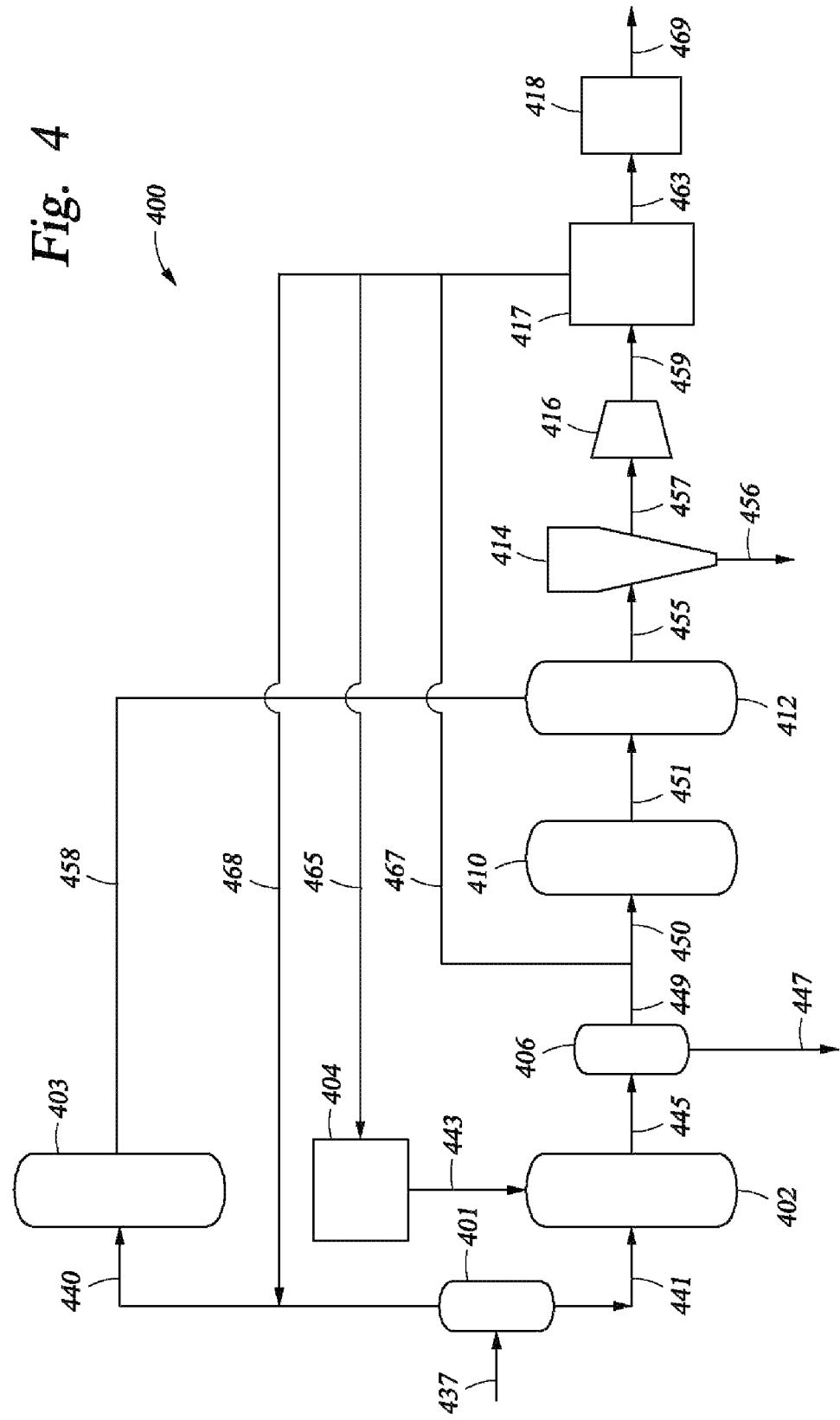
FIG. 4 is a simplified diagrammatic illustration of another exemplary process for converting a hydrocarbon feed to conversion products in accordance with an embodiment of the present techniques.

FIG. 4 is a simplified diagrammatic illustration 400 of still yet another exemplary process for convert hydrocarbon feed into conversion products in accordance with an embodiment of the present techniques. In this process, separators and a hydrotreater may be utilized to process a hydrocarbon feed being provided to the pyrolysis reactors 403 and 410. The feed preparation stage may include a first separation unit 401, a hydrotreater 402, a gas heater 404 and a second separation unit 406, while the cracking stage may include the first pyrolysis reactor 403 or a second pyrolysis reactor 410. The recovery stage may include a combining unit 412, a solids removal unit 414, a compressor 416, a third separation unit 417, and a converter 418. Again, similar to the discussion related to FIGS. 2 and 3, various units in this configuration may operate and function in a substantially similar manner to the units noted above in FIGS. 2 and 3.

To begin, a hydrocarbon feed may be provided via line 437 to the first separation unit 401. The separation unit 401 may be used to separate the hydrocarbon feed into a vapor product (e.g., a hydrogen-rich hydrocarbon feed for the first pyrolysis feed) and a bottoms product (e.g., a hydrogen deficient hydrocarbon feed, high boiling materials, or other solids and liquids). Examples of equipment suitable for separating the vapor product from the liquid product include a knockout drum (e.g., substantially any vapor-liquid separator), a flash drum, distillation column/unit, flash drum having a heating means within the drum, a knockout drum having heating means within the knock-out drum, and combinations thereof. During separation the temperature of the separation unit 401 is maintained between 50° C. to 750° C. or preferably 100° C. to 515° C., which may be adjusted to control the separation level within the separation unit 401. Depending on the hydrocarbon feed, the vapor product (e.g., the hydrogen-rich hydrocarbon feed) may be readily separated from the remaining hydrocarbon feed. The liquid product, which may include non-volatiles, may be withdrawn or removed from the separation unit 401 as a bottoms product or stream via line 441. The vapor product may be withdrawn from separation unit 401 as an overhead stream. The overhead stream may be combined with a recycle product provided from line 468 and passed via line 440 to the first pyrolysis reactor 403 as first pyrolysis feed. The first pyrolysis feed includes at least a fraction of the vapor product and may optionally be adjusted to have a hydrogen content within a predetermined range by addition of diluent and/or recycle feeds, as noted above.

The first pyrolysis feed may be provided to the first pyrolysis reactor 403 via line 440. Similar to the discussion above, the first pyrolysis reactor 403 may include any of the other high-severity pyrolysis reactors. Once cracked, the first reactor product from the first pyrolysis reactor 403 may be further processed in the recovery stage, in a similar manner to the discussion above for FIGS. 2 and 3. This first reactor product may be passed to the combining unit 412 via line 458. The combining unit 412 may be a manifold, a mixing vessel, a line coupling or other suitable region or coupling of these reactor products from the respective reactors.

From the first separator unit 401, the hydrogen deficient feed may be provided via line 441 to the hydrotreater 402. The hydrogen deficient feed may include resid, such as crude, atmospheric resid, vacuum resid, and/or other streams containing asphaltenese, for example. Along with the hydrogen deficient feed, a heated recycle product may be provided to the hydrotreater 402 via line 443. The heated recycle product may include methane, hydrogen or any combination thereof.

The hydrotreater 402 may be a high-severity hydrotreater. This hydrotreater 402 may be configured to add hydrogen to break up heavy molecules, which includes using hydrogen to separate aromatic cores from each other without saturating the aromatic cores (e.g., hydro visbreaking). A preferred hydrotreating unit may be a hydroprocessing unit, such as a hydrovisbreaker, resid hydrocracker or resid hydrotreater that yields significant 565° C. boiling point conversion or non-volatile conversion. The hydrotreating unit may operate at low hydrogen partial pressure to avoid hydrogen incorporation or aromatic saturation. The hydrotreating unit may operate at pressures between 200 psig and 2000 psig (between 1379 kPag and 13789 kPag) and at space velocities (LHSV) from 0.1 to ≥20. Hydrogen consumption for the hydrotreating process may be as low as 200 standard cubic feed per barrel (scf/bbl) and as high as 2000 scf/bbl at higher hydrogen pressures. The hydrotreating processes may involve combining the hydrocarbon feed containing non-volatiles with a hydrogen containing stream, which may be a separate stream or a recycle product (e.g., hydrogen product) from the recovery stage. Preferably, the hydrotreating process converts the non-volatile components to lighter volatile hydrocarbons. Non-volatiles (e.g., resid) conversion may be ≥20 wt %, ≥40 wt %, ≥50 wt %, ≥60 wt % or ≥80 wt %. The hydrotreating process may also convert aromatic carbon to aliphatic carbon. Preferably, aromatic carbon conversion is less than the amount of the non-volatile conversion. Hydrotreating or hydrovisbreaking is preferred over visbreaking because hydrotreating increases non-volatiles conversion and reduces downgrading heavier components.

After hydrotreating, the hydrotreated product is provided from the hydrotreater 402 via line 445 to the second separation unit 406. The second separation unit 406 may be a flash drum or other suitable separation device, similar to the separation unit 401. The second separation unit 406 may separate the hydrotreated product into bottoms product and a vapor product. The bottom product may include the non-volatiles, which is conducted away via line 447 for further processing.

In this configuration, the vapor product may then be provided to the second pyrolysis reactor 410 via lines 449 and 450. The second reactor feed in line 449 may be combined with a recycle product provided from line 467 to form the second pyrolysis feed in line 450. Similar to the discussion above, the second pyrolysis reactor 410 may include any of the high-severity pyrolysis reactors, which may preferably be a thermal pyrolysis reactor (e.g., a reverse flow regenerative reactor). Once cracked, the second reactor product from the second pyrolysis reactor 410 may be further processed in the recovery stage, in a similar manner to the discussion above for FIG. 3. Then, this second reactor product may be passed to the combining unit 412 via line 451. The first reactor product and the second reactor product from the respective reactors may be combined in a variety of different manners, as noted above. Then, the combined reactor product may be provided to a solid removal unit 414 via line 455, which removes a bottoms product that is conducted away via line 456 from the remaining reactor product that is provided via line 457 to the compressor 416.

The remaining reactor products may then be provided to the compressor 416, which may operate similar to the compressors noted above. The compressed reactor product may then be provided via line 459 to the third separation unit 417. The third separation unit 417 may separate light gas products and heavier products, as noted above. The third separation unit 417 may include a hydrogen separation unit to separate the recycle product, such as hydrogen and/or methane, from the remaining reactor product. The recycle product may be provided via line 465 to a gas heater 404, may be provided via line 467 to the vapor product from the second separation unit 406, or may be provided via line 468 to the first pyrolysis reactor 403. The recycle product may be hydrogen, methane, a combination thereof or other suitable products as noted above. The separation may produce light gas streams that are enriched in hydrogen ($H_2$) gas and streams that are enriched in light saturated hydrocarbons such as methane gas. Streams that are $H_2$-enriched may be recycled to the hot gas heater via line 465, more may be recycled to either pyrolysis reactor as diluent, for example may be recycled to the second pyrolysis reactor via line 467 as diluent for hydrogen-deficient hydrocarbon feed. Streams that are enriched in light saturated hydrocarbons such as methane may be recycled to either reactor as diluent, and may be recycled to the first pyrolysis reactor via line 468 as a component of the hydrogen-rich hydrocarbon feed. The remaining reactor product, enriched in acetylene, may be passed via line 463 to the converter 418, which may operate similar to the converters discussed above. The remaining reactor product may be processed in the converter 418 and the conversion product may be provided via line 469 to the other upgrading unit (not shown), which may operate similar to the purification and upgrading units noted above.

This configuration may be utilized to further enhance the processing of a hydrocarbon feed by dividing the hydrocarbon feed into a hydrogen deficient feed for the second pyrolysis reactor and supplementing the hydrogen deficient feed with a recycle product from at least a portion of the first reactor product, which may also include recycle product from at least a portion of the second reactor product. For instance, the process takes a lower value feed having a higher average boiling curve and converts this into chemical products, such as ethylene, instead of using these feeds as fuel. As a result, combustible non-volatiles may be converted into volatiles and thereby utilized as a hydrocarbon feed for this process.

Although the units of FIGS. 2 to 4 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 to 4.

Each of the pyrolysis reactors may be operated at different temperatures and pressures based on the specific operation and process variations. The different pyrolysis reactors may include specific mechanisms and processes to heat the pyrolysis feeds. As such, each pyrolysis reactor and/or separation unit may include different means for measuring the temperature of that specific process.

Accordingly, in one or more of the embodiments, a control mechanism may be utilized to manage the separation of the hydrocarbon feed into the pyrolysis feeds. The control mechanism may include a process control unit coupled to one or more measurement devices that measure operational data (e.g., temperature, hydrogen content, composition, pressure, and the like) and one or more control units for adjusting operational settings (e.g., amount fuel provided to the pyrolysis reactors, pressure for the different units or the like). The process control unit, measurement devices and/or control units may communicate with each other via a physical and/or wireless means.

The process control unit may include a computer system along with one or more monitors and input/output components. The computer system may include memory to store sets of instructions and operational data and a processor to execute the instructions and access the operational data. In this system, operational settings may be adjusted to manage or refine the processing of the feeds within the system and to manage the operating parameters. For instance, operational settings may be adjusted in the system to further refine the separation of the hydrocarbon feed into the products or feeds, such as the first pyrolysis feed and the second pyrolysis feed. These operating parameters may include monitored values, which are stored as operational data in the memory, and utilized by the processor in executing one or more sets of instructions to monitor the flow of hydrocarbons through the system, to adjust operational settings, and other similar operations.

Along with the process control unit, the control mechanism may include different types of measurement devices, such as a temperature measurement device and a hydrogen measurement device. The temperature measurement device, which may include a thermocouple or pyrometer, may be configured to measure the temperature of the hydrocarbon feed prior to the separation unit, the temperature of the products from the separation unit, temperature of the pyrolysis feeds prior to the respective pyrolysis reactor. The hydrogen measurement device, which may include densitometer, nuclear magnetic resonance (NMR) spectrometer or offline gravimetric analyzer (ASTM D1018, D3343, D4808, D5291, D7171) and may be configured to measure the hydrogen content of the feeds, such as the hydrocarbon feed, first pyrolysis feed, and second pyrolysis feed.

The one or more control units may include different control units to adjust different operational settings. For example, a dilution control unit may be utilized and configured to adjust the amount of a dilution or recycle fluid mixed into the first pyrolysis feed or the second pyrolysis feed prior to being passed to the respective pyrolysis reactor and/or the hydrocarbon feed prior to the separation unit.

The present techniques may monitor certain operating parameters and adjust operational settings to provide an enhanced process. For instance, the control mechanism may include a hydrogen measurement device configured to measure hydrogen content of the first pyrolysis feed prior to the first pyrolysis reactor. The control mechanism may also include a process control unit having a set of instructions stored in memory and accessed via a processor, which are configured to (i) receive operational parameters from the hydrogen measurement device; (ii) to calculate the amount of diluent feed; and provide an indication to a diluent control unit to adjustment to the flow rate of the recycle stream based on the determined flow rate.

To provide the separation, operating parameters may be monitored and adjusted to vary the separation level. The operating parameters may include temperature of the hydrocarbon feed, pressures within different vessels along the flow path to the separator or within the separator. These operating parameters may be monitored, stored in memory as operational data, and utilized to adjust operational settings, which may be stored in memory, via a computer system. The determination of the separation level may be calculated by the computer system in the process control unit, prior to the hydrocarbon feed being provided to the separator, prior to offloading the feed, or prior to purchasing the hydrocarbon feed. Further, the determination of the separation level may be adjusted in real time or concurrently with the processing of the hydrocarbon feed, depending on the specific configuration.

Based on the operational data from these measuring devices, the computer system of the process control unit may calculate a separation level or access a previously determined separation level. A comparison of the operational data (e.g., flow rates for this example) and the desired separation level may be performed, which may be a difference comparison or other suitable comparison. Based on the comparison, the computer system of the process control unit may adjust the flow valves coupled along the lines to increase or decrease the flow. As another possible adjustment, if the separation unit is a manifold or other device with one or more valves for each of the light fraction streams and/or the heavy fraction streams, the control mechanism may adjust the different distillates being routed to the respective pyrolysis reactor. Accordingly, in this configuration, the flow rate may be used to manage the separation level.

As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

The term "peak pyrolysis gas temperature" means the maximum temperature achieved by the bulk pyrolysis stream gases as they travel through the pyrolysis reactor (e.g., cracking region or radiant region). For thermal pyrolysis, wherein the heat is predominantly provided by heat transfer via solid surfaces, this temperature may be a temperature within a tubular or channel that carries the pyrolysis stream. For regenerative thermal pyrolysis reactors, this temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checkerbrick, tile or honeycomb solid material, or within a furnace tubular, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

The one or more embodiments may include the conversion of feedstocks into higher value hydrocarbons, such as acetylene, at different temperatures. These temperatures may include high reformation temperature, which in the past has been a significant barrier to commercialization and efficiency. The pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of ≤about 815° C., which corresponds to the peak pyrolysis gas temperature. However, in the present techniques, the thermal pyrolysis reactor may operate at peak pyrolysis gas temperatures between 1200.0° C. and 2200.0° C., preferably between 1400.0° C. to 1900.0° C. In particular, for reactors with an isothermal heat profile, the temperatures may be between 1450° C. and 1700° C., or between at least 1540° C. to 1650° C. For reactors with a Gaussian like heat profile, the peak pyrolysis gas temperatures may be between 1450.0° C. and 1900.0° C. and/or 1540.0° C. and 1800.0° C. In some reactions, it may even be still more preferable to expose the pyrolysis feed to heat using very short residence times, such as ≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred process may pyrolyze the feed stream within the reactor, such as at peak pyrolysis gas temperatures of from 1540.0° C. to 2200.0° C., and more preferably from 1600.0° C. to 1800.0° C. Exemplary residence times preferably may be short, such as ≤0.5 second, ≤0.3 second and preferably ≤ about 50 milliseconds or in the range of 0.5 seconds to 0.001 seconds. High severity residence times are preferably ≤0.05 seconds, and more preferably less than 0.02 seconds.

As described earlier, achieving any peak pyrolysis gas temperature for certain embodiments involves the existence of a solid temperature that is heated to a higher temperature, and a combustion gas temperature that is a higher temperature than the solid temperature. In one or more embodiments of the present techniques, the maximum temperature of the solid elements in the thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in the thermal pyrolysis system is between 10° C. and 100° C. higher than the peak pyrolysis gas temperature. Reverse flow regenerative reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

In one or more embodiments, the hydrocarbon feed may include different hydrocarbon components or mixtures thereof. For instance, the hydrocarbon feed may include methane, which may be part of a natural gas stream. This feed, including associated hydrocarbon and impurity gases, may be supplied into the reactor system. The supplied feed may be sweetened and/or dehydrated natural gas. Natural gas commonly includes various concentrations of associated gases, such as ethane and other alkanes, preferably in lesser concentrations than methane. The supplied natural gas may include impurities, such as hydrogen sulfide $H_2S$ and nitrogen. Certain embodiments may also serve to simultaneously convert some fraction of the associated higher hydrocarbons to acetylene. In other embodiments, the present techniques and compositions may be utilized with liquid feeds, such a vacuum gas oil (VGO) or naphthas.

In other embodiments, the first pyrolysis reactor may be a regenerative reverse flow reactor or regenerative pyrolysis reactor. As example, U.S. Ser. No. 61/226,499, which is incorporated by reference, describes a process and regenerative pyrolysis reactor utilized for pyrolyzing a resid-containing hydrocarbon feedstock. Further, other examples of such reactors may be found in U.S. Patent Application Publication Nos. 2007/0144940 and 2008/0142409. These references, which are incorporated by reference, teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto. Other examples may be found in U.S. Patent Application Publication No. 2007/0191664, 2009/0008292 and 2009/008292; U.S. Pat. No. 7,491,250; and U.S. patent application Ser. Nos. 61/349,464, 12/119,762, 12/121,353, which are each incorporated by reference.

As an example, U.S. Ser. No. 11/643,541 (U.S. Patent Application Publication No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising primary end and a secondary end, the first and second reactors oriented in a series relationship with respect to each other such that the secondary end of the second reactor is proximate the second end of the first reactor. The process may include a two-step process wherein heat is (1) added to the reactor media via in-situ combustion step and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step, which may be carried out at a pressure between about 5 pounds per square inch absolute (psia) (35 kPa absolute (kPaa)) up to about 45 psia (310 kPaa), supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 $ft^{-1}$, heat transfer coefficient $\geq 0.02$ $cal/cm^3s°$ C., and bulk heat capacity $\geq$ about 0.10 $cal/cm^{3o}$ C., and may be comprised of honeycomb monoliths having 40 to 80% open frontal area and between about 50 and 2000 channels per square inch. The process may further include compressors, blowers, or fans to supply air as one combustion feed during the combustion step, which may be carried out at a pressure between about 15 psia (103 kPaa) and 45 psia (310 kPaa); may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Noncombustible gases, for example $H_2O$, $CO_2$, and $N_2$, may be added to the combustion feed to reduce combustion temperature. The combustion step may comprise a first and second reactant that are a fuel gas and an oxidant that are maintained substantially separated as they pass through the first reactor and which combust or burn when combined. By substantially separated is meant that at least 50%, and more preferably 75% or 90% of the potential combustion that may occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume 20% of the total volume of mixer plus flow regions in first and second reactor, and preferably has a geometric void volume $\leq 20\%$ of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps have equal durations.

In some other embodiments, the use of the materials may provide additional benefits in the selectivity of operations. For example, regenerative pyrolysis reactors have generally have not been used commercially to temperatures above 1300° C. because the alumina internals are generally incompatible with processes operating at such high temperatures. In a regenerative reactor, the operating temperatures within the reactor may reach temperatures up to 1500° C. to 2200° C. In this manner, the pyrolysis reactors materials have to be designed with withstand these temperature swings. That is, in the proposed configuration, pyrolysis reactors may have components or internals, such as valves, tubes, conductive monoliths, thin-walled honeycombs, bead-beds, mixers, quench media, and other reactor components, regardless of whether simple or complex shaped, that are directly associated with the pyrolysis reaction. These components made of different materials (e.g., substantially, predominately or partially made from a refractory material) may be able to withstand these larger temperature swings. As a specific example, U.S. Ser. Nos. 12/099,251; 12/277,056; 12/467, 832; 12/772,757; and 12/623,046; which are each incorporated by reference, describe different material that may be used in a pyrolysis reactor.

The embodiments of the present techniques may also comprise different embodiments, such as in the following exemplary paragraphs:

1. A hydrocarbon conversion method comprising: exposing a first pyrolysis feed in a first pyrolysis reactor to a peak pyrolysis gas temperature ≥1400.0° C. to produce a first reactor product, wherein the first pyrolysis feed has a hydrogen content ≥14.0 wt % based on the weight of hydrocarbon in the pyrolysis feed; exposing a second pyrolysis feed in a second pyrolysis reactor to a peak pyrolysis gas temperature ≥1400.0° C. to produce a second reactor product having ≥0.5 wt % methane based on the weight of the second reactor product, wherein the second pyrolysis feed has a hydrogen content <14.0 wt % based on the weight of hydrocarbon in the pyrolysis feed; and separating hydrogen ($H_2$) from at least a portion of the first reactor product, wherein the second pyrolysis feed comprises at least a portion of the separated hydrogen; and separating methane from at least a portion of the second reactor product, wherein the first pyrolysis feed comprises at least a portion of the separated methane.
2. The method of paragraph 1, further comprising combining the at least a portion of the first reactor product with the at least a portion of the second reactor product.
3. The method of paragraph 1 or 2, wherein the one or more of the first reactor product and second reactor product has a $C_3^+$ to acetylene weight ratio ≤0.5.
4. The method of any one of paragraphs 1 to 3, wherein the first pyrolysis feed comprises ≥50.0 wt % of hydrocarbon, the hydrocarbon having a hydrogen content ≥14.0 wt %.
5. The method of any one of paragraphs 1 to 3, wherein the second pyrolysis feed comprises ≥50.0 wt % of hydrocarbon, the hydrocarbon having a hydrogen content of the hydrocarbons that is ≤14.0 wt %.
6. The method of any one of paragraphs 1 to 3, wherein at least 50 wt % of the hydrocarbon of the second pyrolysis feed have a hydrogen content ≤10.0 wt %.
7. The method of any one of paragraphs 1 to 6, wherein the second pyrolysis feed comprises a first recycle product, the first recycle product comprising ≥30.0 wt % hydrogen ($H_2$) based on the weight of the first recycle product, at least a portion of the first recycle product's hydrogen being derived from the separated hydrogen.
8. The method of paragraph 7, wherein the first recycle product comprises ≥50.0 wt % hydrogen based on the weight of the first recycle product.
9. The method of any one of paragraphs 1 to 8, wherein the first pyrolysis feed comprises a second recycle product, the second recycle product comprising (i) ≥30.0 wt % methane based on the weight of the second recycle product and/or (ii) ≥30.0 wt % ethane based on the weight of the second recycle product; wherein at least a portion of the second recycle product's methane is derived from the separated methane.
10. The method of paragraph 9, wherein the second recycle product comprises ≥50.0 wt % methane based on the weight of the second recycle product.
11. The method of any of paragraphs 1 and 10, wherein one or more of the first reactor product and the second reactor product have a $C_3^+$ to acetylene weight ratio ≤0.45.
12. The method of any one of paragraphs 1 to 11, wherein the peak pyrolysis gas temperature of the first pyrolysis reactor is ≥1540.0° C. and the peak pyrolysis gas temperatures of the second pyrolysis reactor is ≥1540.0° C.
13. The method of any one of paragraphs 1 to 11, wherein the peak pyrolysis gas temperature of the first pyrolysis reactor is ≥1600.0° C.
14. The method of any one of paragraphs 1 to 13, wherein the first pyrolysis feed and the second pyrolysis feed are derived from at least one hydrocarbon feed.
15. The method of any one of paragraphs 1 to 14, wherein the peak pyrolysis gas temperature of the first pyrolysis reactor is ≥1700.0° C.
16. The method of any of paragraphs 1 to 15, further comprising combining at least a portion of the first reactor product with at least a portion of the second reactor product and converting at least a portion thereof to produce a conversion product.
17. The method of paragraph 16, further comprising: separating a light gas product from the combined reactor products to form an acetylene rich product; and converting at least a portion of the acetylene-rich product to produce a conversion product.
18. The method of paragraph 16, further comprising polymerizing at least a portion of the conversion product to produce polyethylene and/or polypropylene.
19. The method of any one of paragraphs 1 to 18, further comprising separating a bottoms product comprising tars and/or solids from the at least a portion of the first reactor product.
20. The method of any one of paragraphs 1 to 19, wherein the separated hydrogen is separated from the first reactor product via one or more of a hydrogen membrane, pressure swing adsorption, electrochemical, cryogenic separation and solvent absorption.
21. The method of paragraph 9, further comprising adding to a combustion feed (i) a portion of the first or second recycle product to produce a first combustion mixture and/or (ii) a portion of the first or second recycle product to produce a second combustion mixture, and then conducting at least one of (a) the first combustion mixture to the first pyrolysis reactor for reacting therein or (b) the second combustion mixture to the second pyrolysis reactor for reacting therein.
22. The method of any one of paragraphs 1 to 20, wherein the peak pyrolysis gas temperature of the first pyrolysis reactor is in the range of 1540.0° C. to 2200.0° C., and wherein the exposing is for a residence time in the range from 0.5 second to 0.001 second.
23. The method of any one of paragraphs 1 to 20, wherein the peak pyrolysis gas temperature is in the range of 1600.0° C. to 1800.0° C., and wherein the exposing is for a residence time in the range from 0.5 second to 0.001 second.

24. The method of any one of paragraphs 1 to 20, wherein the first pyrolysis reactor is a regenerative reverse flow reactor that comprises a reactor body, wherein the reactor body forms a reaction region within the reactor body; a packing material disposed at least partially within the reaction region; and one or more poppet valve assemblies coupled to the reactor body and in flow communication with the reaction region and controlling fluid flow of the at least a portion of the first pyrolysis feed between a location external to the reactor body and within the reaction region.

25. The method of any one of paragraphs 1 to 20 further comprising: exothermically reacting first and second combustion feeds to heat a region at least partially within the first pyrolysis reactor; removing combustion products from the first pyrolysis reactor; and heating the first pyrolysis feed using at least a portion of the heat generated by the exothermic reaction.

26. The method of paragraph 25, further comprising: exothermically reacting third and fourth combustion feeds in the second pyrolysis reactor to form combustion products and heat a region within the second pyrolysis reactor; removing the combustion products from the second pyrolysis reactor; and passing the at least a portion of the second pyrolysis feed into the region within the second pyrolysis reactor to heat the at least a portion of the second pyrolysis feed.

27. The method of paragraph 26, further comprising purging the region with a vapor purge stream after the removing the combustion products and prior to passing the at least a portion of the first pyrolysis feed into the region.

28. The method of paragraph 25, wherein the first combustion feed and the second combustion feed are separately heated within the first pyrolysis reactor prior to exothermically reacting in the region.

29. The method of any one of paragraphs 1 to 28, further comprising: measuring the hydrogen content of a second reactor feed prior to the second pyrolysis reactor; calculating a hydrogen deficiency amount of a second reactor feed having a hydrogen content, the hydrogen content being determined before pyrolysis; adjusting the hydrogen content to form the second pyrolysis feed based on the calculated hydrogen deficiency amount.

30. The method of any one of paragraphs 1 to 28, wherein (a) the first pyrolysis feed is formed by: hydrotreating a hydrogen deficient feed, the hydrocarbon deficient feed being derived from a hydrocarbon feed, wherein the hydrotreating utilizes at least a portion of the separated hydrogen; and separating a bottoms product comprising solids from the hydrotreated feed; and (b) the second pyrolysis feed is derived from at least a portion of the bottoms product.

31. The method of any one of paragraphs 1 to 28, further comprising: separating the first pyrolysis feed and the second pyrolysis feed from a hydrocarbon feed; measuring temperature of the hydrocarbon feed; and adjusting the separation conditions based at least partially on the measured temperature.

32. The method of paragraph 1, wherein the first pyrolysis reactor and second pyrolysis reactor are each regenerative reverse flow thermal pyrolysis reactors.

33. The method of paragraph 1, wherein the first pyrolysis reactor and second pyrolysis reactor are each partial oxidation reactors.

34. The method of paragraph 1, wherein the first pyrolysis reactor and second pyrolysis reactor are each arc reactors.

35. An apparatus for processing hydrocarbons comprising: a first pyrolysis reactor configured to expose a first pyrolysis feed to peak pyrolysis gas temperatures $\geq 1400.0°$ C. to produce a first reactor product; a second pyrolysis reactor configured to expose a second pyrolysis feed to peak pyrolysis gas temperatures $\geq 1400.0°$ C. to produce a second reactor product; and a separation unit in fluid communication with the first pyrolysis reactor, the separation unit being configured to separate a recycle product from at least a portion of the first reactor product; a mixing unit in fluid communication with the second pyrolysis reactor and the separation unit, the mixing unit being configured to combine at least a portion of the recycle product with a second reactor feed to form the second pyrolysis feed.

36. The apparatus of paragraph 35, further comprising a combining unit in fluid communication with the separation unit and the second pyrolysis reactor, the combining unit being configured to combine the at least a portion of the first reactor product and at least a portion of the second reactor product into a combined reactor product.

37. The apparatus of paragraph 35, further comprising a combining unit in fluid communication with the first pyrolysis reactor and the second pyrolysis reactor, the combining unit being configured to combine the at least a portion of the first reactor product and at least a portion of the second reactor product into a combined reactor product.

38. The apparatus of any one of paragraphs 36 to 37, further comprising a compressor in fluid communication with the combining unit, the compressor being configured to compress at least a portion of the combined reactor product.

39. The apparatus of any one of paragraphs 36 to 37, further comprising a solids removal unit in fluid communication with the combining unit, the solids removal unit being configured to separate a bottoms product comprising tars and/or solids from the at least a portion of the first reactor product.

40. The apparatus of any one of paragraphs 36 to 37, further comprising a converter in fluid communication with the combining unit, the converter being configured to convert at least a portion of the combined reactor product into a conversion product.

41. The apparatus of paragraph 40, further comprising a polymerization unit in fluid communication with the converter, the polymerization unit being configured to convert at least a portion of the conversion product into polyethylene.

42. The apparatus of any one of paragraphs 35 to 41, wherein the separation unit comprises at least one of a hydrogen membrane, a pressure swing adsorption unit, an electrochemical unit, a cryogenic separation unit, a solvent absorption unit and any combination thereof.

43. The apparatus of any one of paragraphs 35 to 42, further comprising one or more lines providing fluid communication between the separation unit and the one or more of the first pyrolysis reactor and the second pyrolysis reactor, at least one of the lines being configured to combine a portion of the recycle product with a combustion feed and react the portion of the recycle product and the combustion feed within the one or more of the first pyrolysis reactor and the second pyrolysis reactor.

44. The apparatus of any one of paragraphs 35 to 42, further comprising one or more lines providing fluid communication between the separation unit and the one of the first pyrolysis reactor, the second pyrolysis reactor and any combination thereof, at least one of the lines being configured to combine a portion of the recycle product with one or more of a first reactor feed and second reactor feed, wherein the first pyrolysis feed is derived from the first reactor feed and the second pyrolysis feed is derived from the second reactor feed.

45. The apparatus of any one of paragraphs 35 to 44, wherein the first pyrolysis reactor is configured to expose the first pyrolysis feed to a peak pyrolysis gas temperature in the range of 1600.0° C. to 1800.0° C., and maintain the at least a portion of the first pyrolysis feed within the first pyrolysis reactor for a residence time in the range of 0.5 seconds to 0.001 seconds.

46. The apparatus of any one of paragraphs 35 to 45, wherein the first pyrolysis reactor comprises at least one reverse flow regenerative pyrolysis reactor, the reverse flow regenerative reactor comprising: a reactor body, wherein the reactor body forms a reaction region within the reactor body; a packing material disposed at least partially within the reaction region; and one or more poppet valve assemblies coupled to the reactor body and in flow communication with the reaction region and configured to control fluid flow of the at least a portion of the first pyrolysis feed between a location external to the reactor body and within the reaction region.

47. The apparatus of any one of paragraphs 35 to 46, further comprising a feed separation unit in fluid communication with the first pyrolysis reactor and the second pyrolysis reactor, the feed separation unit being configured to separate a hydrocarbon feed into a first reactor feed and a second reactor feed, wherein the first pyrolysis feed is derived from the first reactor feed and the second pyrolysis feed is derived from the second reactor feed.

48. The apparatus of any one of paragraphs 35 to 47, further comprising: a hydrotreating unit configured to receive a hydrogen deficient feed and a heated recycle product and convert the hydrogen deficient feed with the heated recycle product to form a hydrotreated product, wherein the first pyrolysis feed is derived from the hydrotreated product; and a heating unit in fluid communication with the separation unit and configured to heat the recycle product prior to providing the recycle product to the hydrotreating unit.

49. The apparatus of paragraph 48, further comprising a feed separation unit in fluid communication with the hydrotreater and the second pyrolysis reactor, the feed separation unit being configured to separate the hydrotreated product into the second reactor feed and a bottoms product.

50. The apparatus of paragraph 35, wherein the first pyrolysis reactor and second pyrolysis reactor are each partial oxidation reactors.

51. The apparatus of paragraph 35, wherein the first pyrolysis reactor and second pyrolysis reactor are each arc reactors.

52. The apparatus of paragraph 35, wherein the first pyrolysis reactor and second pyrolysis reactor are each thermal pyrolysis reactors.

53. The apparatus of any one of paragraphs 35 to 52, further comprising: (a) a hydrogen measurement device in fluid communication with the second pyrolysis reactor, the hydrogen measurement device being configured to measure the hydrogen content of the second reactor feed prior to the second pyrolysis reactor; and (b) a process control unit in communication with the hydrogen measurement device, the process control unit being configured to: (i) calculate a hydrogen deficiency amount based on the hydrogen content of the second reactor feed; and (ii) communicate an adjustment to the hydrogen content of the second reactor feed based on the calculated hydrogen deficiency amount.

54. The apparatus of paragraph 35, comprising a hydrogen control unit in communication with the process control unit, the hydrogen control unit being configured to adjust the hydrogen content of the second reactor feed based on the communication with the process control unit.

While the present invention has been described and illustrated with respect to certain embodiments, it is to be understood that the invention is not limited to the particulars disclosed and extends to all equivalents within the scope of the claims.

The invention claimed is:

1. A hydrocarbon conversion method comprising:
exposing a first pyrolysis feed in a first pyrolysis reactor to a peak pyrolysis gas temperature in the range of from 1540° C. to 2200° C., a pressure ≥44 psig, and a residence time in the range of from 0.004 seconds to 0.050 seconds to produce a first reactor product having a $C_{3+}$: acetylene weight ratio in the range of from 0.261 to 0.5, a $C_{3+}$ amount ≤12.9 wt %, and a surplus hydrogen amount ≥10.3 wt. %, wherein (i) the first pyrolysis feed comprises ≥50.0 wt % of hydrocarbons, the hydrocarbons having a hydrogen content ≤14.0 wt %, and (ii), the first pyrolysis reactor is a regenerative reverse-flow thermal pyrolysis reactor;
exposing a second pyrolysis feed in a second pyrolysis reactor to a peak pyrolysis gas temperature ≥1400.0° C. to produce a second reactor product having ≥0.5 wt % methane based on the weight of the second reactor product, wherein the second pyrolysis feed has a hydrogen content <14.0 wt % based on the weight of hydrocarbons in the second pyrolysis feed;
separating at least a portion of the surplus hydrogen from at least a portion of the first reactor product, wherein the second pyrolysis feed comprises at least a portion of the separated surplus hydrogen; and
separating methane from at least a portion of the second reactor product, wherein the first pyrolysis feed comprises at least a portion of the separated methane.

2. The method of claim 1, further comprising combining the at least a portion of the first reactor product with the at least a portion of the second reactor product.

3. The method of claim 1, wherein the second reactor product has a $C_{3+}$ to acetylene weight ratio ≤0.5.

4. The method of claim 1, wherein the hydrocarbons of the first pyrolysis feed include methane.

5. The method of claim 1, wherein at least 50 wt % of the hydrocarbons of the second pyrolysis feed have a hydrogen content ≤10.0 wt %.

6. The method of claim 1, wherein the second pyrolysis feed comprises a first recycle product, the first recycle product comprising ≥30.0 wt % hydrogen gas based on the weight of the first recycle product, at least a portion of the hydrogen gas in the first recycle product being derived from the separated surplus hydrogen.

7. The method of claim 6, wherein the first pyrolysis feed comprises a second recycle product, the second recycle product comprising ≥30.0 wt % methane based on the weight of the second recycle product, wherein at least a portion of methane in the second recycle product is derived from the separated methane.

8. The method of claim 1, wherein the peak pyrolysis gas temperature of the first pyrolysis reactor is in the range of from 1600.0° C. to 2200° C.

9. The method of claim 1, further comprising combining at least a portion of the first reactor product with at least a portion of the second reactor product and converting at least a portion of the combined reactor products to produce a conversion product.

10. The method of claim 9, comprising polymerizing at least a portion of the conversion product to produce polyethylene and/or polypropylene.

11. The method of claim 7, further comprising adding to a combustion feed (i) a portion of the first or second recycle product to produce a first combustion mixture and/or (ii) a portion of the first or second recycle product to produce a second combustion mixture, and then conducting at least one of (a) the first combustion mixture to the first pyrolysis reactor for reacting therein or (b) the second combustion mixture to the second pyrolysis reactor for reacting therein.

12. The method of claim 1, further comprising:
   measuring the hydrogen content of a second reactor feed upstream of the second pyrolysis reactor;
   calculating a hydrogen deficiency amount of the second reactor feed having a hydrogen content, the hydrogen content being determined before pyrolysis;
   adjusting the hydrogen content to form the second pyrolysis feed based on the calculated hydrogen deficiency amount.

13. The method of claim 1, wherein the second pyrolysis reactor is a regenerative reverse flow thermal pyrolysis reactor.

14. The method of claim 1, wherein the second pyrolysis reactor is a partial oxidation reactor.

15. The method of claim 1, wherein the pressure in the first pyrolysis reactor is $\geq 103$ psig.

\* \* \* \* \*